(12) United States Patent
Takenaka et al.

(10) Patent No.: US 10,548,757 B2
(45) Date of Patent: Feb. 4, 2020

(54) JOINT MECHANISM

(71) Applicant: HONDA MOTOR CO., LTD., Tokyo (JP)

(72) Inventors: Toru Takenaka, Saitama (JP); Hiroshi Gomi, Saitama (JP); Yuichi Uebayashi, Saitama (JP); Yosuke Ikedo, Saitama (JP); Kenichi Katagiri, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 320 days.

(21) Appl. No.: 14/570,275

(22) Filed: Dec. 15, 2014

(65) Prior Publication Data

US 2015/0182366 A1 Jul. 2, 2015

(30) Foreign Application Priority Data

Dec. 27, 2013 (JP) ................. 2013-271187

(51) Int. Cl.
*A61F 5/00* (2006.01)
*A61F 5/01* (2006.01)

(52) U.S. Cl.
CPC .... *A61F 5/0123* (2013.01); *A61F 2005/0141* (2013.01); *A61F 2005/0148* (2013.01); *A61F 2250/0012* (2013.01)

(58) Field of Classification Search
CPC .......... A61H 1/00; A61H 1/02; A61H 1/0247; A61H 1/0248; A61H 1/0251; A61H 1/0255; A61H 1/0259; A61H 1/0262; A61H 1/0214; A61H 1/0237; A61H 1/074; A61H 1/0277; A61H 1/0281; A61H 1/0285; A61H 1/028; A61H 1/0274; A61H 2001/0203; A61H 2001/0207; A61H 2001/0211; A61H 2001/0248; A61H 2001/0251; A61H 2201/16; A61H 2201/1652; A61H 2201/1657; A61H 2201/1664;
(Continued)

(56) References Cited

U.S. PATENT DOCUMENTS 4,393,542 A * 7/1983 Martinez ............... A61F 5/0123
16/369
4,467,792 A * 8/1984 Young ................... A61F 13/041
602/16

(Continued)

FOREIGN PATENT DOCUMENTS

JP 07-116207 5/1995
JP 2010-012328 1/2010
(Continued)

OTHER PUBLICATIONS

Japanese Office Action dated Jan. 5, 2016, 6 pages.

*Primary Examiner* — Keri J Nelson
*Assistant Examiner* — Adam Baker
(74) *Attorney, Agent, or Firm* — Rankin, Hill & Clark LLP

(57) ABSTRACT

A joint mechanism 4 has a zigzag structure 13 extending in a zigzag pattern between a first member 11 and a second member 12. A flexible lengthy member 16 fixed to the first member 11 extends from the first member 11 toward the second member 12 and is travelable with respect to the second member 12. A tension application unit 30 that applies a tension to the flexible lengthy member 16 is configured to be capable of changing a tension to apply.

27 Claims, 11 Drawing Sheets

(58) Field of Classification Search
CPC .............. A61H 2201/1676; A61H 3/00; A61H 2003/007; A61F 5/00; A61F 5/0102; A61F 5/0123; A61F 5/0125; A61F 2005/0141; A61F 2005/0146; A61F 2005/0148; A61F 2005/0153; A61F 2005/0158; A61F 2005/016; A61F 2250/0012
USPC .......................................... 602/51, 6, 23, 26
See application file for complete search history.

(56) References Cited

U.S. PATENT DOCUMENTS

| | | | | | |
|---|---|---|---|---|---|
| 4,522,199 | A | * | 6/1985 | Waddell | A61F 5/0104 602/23 |
| 4,573,455 | A | * | 3/1986 | Hoy | A61F 5/0123 602/16 |
| 4,727,862 | A | * | 3/1988 | Waddell | A61F 5/02 602/16 |
| 5,178,137 | A | * | 1/1993 | Goor | A61F 5/0111 601/40 |
| 7,335,177 | B2 | * | 2/2008 | Reynolds | A61F 5/0127 602/23 |
| 8,235,924 | B2 | * | 8/2012 | Bachmann | A61F 5/0102 602/16 |
| 2006/0211967 | A1 | * | 9/2006 | Reynolds | A61F 5/0102 602/23 |
| 2014/0094728 | A1 | * | 4/2014 | Soderberg | A61F 5/028 602/6 |

FOREIGN PATENT DOCUMENTS

| | | |
|---|---|---|
| JP | 2012-090849 | 5/2012 |
| WO | 2012/125765 | 9/2012 |
| WO | 2013/188868 | 12/2013 |

* cited by examiner

JOINT MECHANISM

BACKGROUND OF THE INVENTION

1. Field of the Invention

The present invention relates to a bendable joint mechanism.

2. Description of the Related Art

Hitherto, as a bendable joint mechanism, there has generally been known one that has a single rotating shaft (joint shaft), i.e. a one-degree-of-freedom rotary type joint mechanism. In this type of joint mechanism, two members are connected so as to be relatively rotatable about a single rotating shaft.

For example, Japanese Patent Application Laid-Open No. 2012-90849 describes a knee joint of a walking assist mechanism that uses the one-degree-of-freedom rotary type joint mechanism described above.

Meanwhile, a joint, such as a human knee joint, does not have a fixed single joint axis, and the position of an instantaneous rotational center changes to accomplish bending at the joint.

Accordingly, an attempt to generate power for assisting the bending and stretching at such a joint by a joint mechanism having a fixed single joint tends to cause a situation in which the motion of a human joint and the motion of the joint of the joint mechanism do not fully match. This frequently causes a person wearing the joint mechanism to feel uncomfortable or awkward mainly due to a force acting to interfere with a desired motion of the joint.

In order to eliminate such an inconvenience, a joint mechanism best suited for each person could be individually prepared, or a structure or the like for connecting a joint mechanism to each person could be designed to be adjustable according to each person.

However, if a dedicated joint mechanism were prepared for each individual, then the joint mechanism would be costly.

Further, if the structure of a joint mechanism were designed to be adjustable for each individual, then the structure of the joint mechanism would tend to be complicated or become larger. In addition, there would be some cases where the joint mechanism could not be satisfactorily suited to each individual, depending on his or her body shape or the like.

SUMMARY OF THE INVENTION

The present invention has been made with a view toward solving the aforesaid problems, and an object of the invention is to provide a joint mechanism capable of generating power for bending, as necessary, by a structure that has a high degree of freedom of bending.

To this end, a power transmission device in accordance with the present invention is a joint mechanism that connects a first member and a second member in a relatively displaceable manner, including:

a zigzag structure which is composed of an elastic member formed between the first member and the second member such that the elastic member extends from the first member toward the second member in a zigzag pattern having an amplitude in a lateral direction, which has an end portion thereof adjacent to the first member and an end portion thereof adjacent to the second member connected to the first member and the second member, respectively, and which is deformably configured to allow the length in the direction of an amplitude centerline thereof and a bending degree of the amplitude centerline to be changed;

a flexible lengthy member which is disposed to extend from the first member toward the second member, which has one end portion adjacent to the first member fixed to the first member, which is provided to be travelable with respect to the second member, and which applies a force for pressing the zigzag structure between the first member and the second member to the zigzag structure in a state in which a tension is being applied; and a tension application unit which is a device for applying a tension to the flexible lengthy member from the other end portion side of the flexible lengthy member and which is configured to be capable of changing the magnitude of the tension (a first aspect of the invention).

In the present invention (including a second to a thirtieth aspects of the invention, which will be discussed hereinafter), the amplitude centerline of the zigzag structure means a line that extends from the first member toward the second member at a central position or a substantially central position of the breadth in an amplitude direction of the zigzag structure. Further, the bending or bending deformation of the zigzag structure means that the zigzag structure deforms such that the amplitude centerline of the zigzag structure bends.

Supplementarily, the zigzag structure is arranged in a row in the zigzag pattern, so that the zigzag structure has one or more top portions on each of both sides in the amplitude direction thereof, and a pair of leg portions that extends in a bifurcated manner from each top portion. Further, in the present invention (including a second to a thirtieth aspects of the invention, which will be discussed hereinafter), a portion of the zigzag structure that is connected to the first member (an end portion adjacent to the first member) or a portion thereof that is connected to the second member (an end portion adjacent to the second member) can be regarded as one top portion. In this case, one of the pair of leg portions that extends in the bifurcated manner from the one top portion is to be regarded as constructed integrally with the first member or the second member.

According to the first aspect of the invention described above, the magnitude of the tension to be applied to the flexible lengthy member by the tension application unit can be adjusted.

In this case, if the tension applied to the flexible lengthy member is zero or small, then the zigzag structure will have a higher degree of freedom of deformation, such as bending deformation, due to the elastic deformation thereof. This makes it possible to change the length of the zigzag structure in the direction of the amplitude centerline or the bending degree of the amplitude centerline in a relatively wide range while maintaining a state in which the elastic force generated by the zigzag structure does not become very large.

In this situation, therefore, the relative displacement between the first member and the second member can be accomplished while controlling the elastic force generated by the zigzag structure between the first member and the second member to a small value.

On the other hand, if the tension applied to the flexible lengthy member is increased to a certain magnitude, then the first member is pressed against the second member through the intermediary of the zigzag structure, thus restricting the deformation of the zigzag structure. The length, in particular, of the zigzag structure in the direction along the flexible lengthy member will be restricted, making it difficult for the zigzag structure to deform such that the length thereof increases.

In this situation, if the relative displacement of the first member and the second member is carried out to bend the zigzag structure (more specifically, to bend the zigzag structure such that one end of the zigzag structure in the amplitude direction is placed on an outer side, while the other end thereof is placed on an inner side), then the zigzag structure will promptly generate an elastic force that works to cancel the bending of the zigzag structure. Further, the elastic force increases with high responsiveness as the bending degree of the zigzag structure, i.e., the bending degree of the amplitude centerline, increases.

Thus, if the relative displacement of the first member and the second member is carried out to bend the zigzag structure by increasing the tension applied to the flexible lengthy member, then the force (moment) that acts to cancel the bending of the zigzag structure can be generated between the first member and the second member by the elastic force of the zigzag structure.

Further, the zigzag structure does not bend about a fixed axis, so that the zigzag structure can be smoothly bent according to the relative displacement of the first member and the second member regardless of whether the relative displacement of the first member and the second member that causes the zigzag structure to bend is a rotational displacement about a single axis.

Hence, the joint mechanism according to the first aspect of the invention is capable of generating power according to the bending, as necessary, by the structure with a high degree of freedom of bending.

In the first aspect of the invention, as the arrangement configuration of the flexible lengthy member, the following arrangement configuration can be adopted. For example, the flexible lengthy member is placed to extend at a position adjacent to one side of both sides in the amplitude direction of the zigzag structure (a second aspect of the invention).

According to the second aspect of the invention, if the zigzag structure is deformed to bend such that one side of both sides in the amplitude direction, which one side is adjacent to the flexible lengthy member, is placed on the outer side and the other side thereof in the amplitude direction is placed on the inner side in a state wherein the tension applied to the flexible lengthy member is relatively high, then an elastic force of a magnitude in a wide range that functions to cancel the bending deformation can be efficiently generated in the zigzag structure.

In the second aspect of the invention, preferably, the joint mechanism further includes an inter-leg-portion elastic member composed of an elastic member provided between a pair of leg portions extending in a bifurcated manner from each of one or more top portions among top portions located on one side in the amplitude direction of the zigzag structure, wherein the inter-leg-portion elastic member is configured such that, upon bending deformation of the zigzag structure in a direction that reduces the interval of the pair of leg portions on both sides of the inter-leg-portion elastic member in a state in which a tension of a predetermined value or more is being applied to the flexible lengthy member by at least the tension application unit, the inter-leg-portion elastic member is compressed between the pair of leg portions so as to generate an elastic force that functions to cancel the bending deformation of the zigzag structure (a third aspect of the invention).

According to the third aspect of the invention, if the zigzag structure is deformed to bend such that each top portion on one side of both sides in the amplitude direction is placed on the outer side and each top portion on the other side in the amplitude direction is placed on the inner side in a state wherein the tension being applied to the flexible lengthy member is relatively high, i.e. a state wherein a tension of a predetermined value or more is being applied, then an elastic force of the inter-leg-portion elastic member is generated in addition to the elastic force of the zigzag structure itself so as to cancel the bending deformation of the zigzag structure.

Thus, in the state wherein the tension applied to the flexible lengthy member is relatively high, the magnitude of the elastic force generated to cancel the bending deformation can be further increased according to the bending deformation of the zigzag structure. This makes it possible to enhance the stiffness, i.e. the stiffness against bending deformation, of the zigzag structure in combination with the inter-leg-portion elastic members.

In the third aspect of the invention, preferably, the inter-leg-portion elastic member is constituted of a first elastic member made of rubber that is firmly fixed to one leg portion of the pair of leg portions on both sides thereof and a second elastic member made of rubber that is firmly fixed to the other leg portion so as to oppose the first elastic member, and the first elastic member and the second elastic member are compressed in contact with each other upon being compressed between the pair of leg portions (a fourth aspect of the invention).

In the foregoing third aspect of the invention, the inter-leg-portion elastic member can be configured such that when, for example, the zigzag structure is deformed to bend while having the rubber inter-leg-portion elastic member firmly fixed to one of the pair of leg portions on both sides thereof (more specifically, if the zigzag structure is deformed to bend such that one side in the amplitude direction thereof is placed on the outer side and the other side is placed on the inner side), the inter-leg-portion elastic member is pressed against the other of the pair of leg portions on both sides thereof so as to compress the inter-leg-portion elastic member.

In such a case, however, when the zigzag structure is deformed to bend, a slide friction attributable to a lateral strain tends to occur between the inter-leg-portion elastic member and the leg portion against which the inter-leg-portion elastic member is pressed, thus easily interfering with smooth bending deformation of the zigzag structure.

In contrast thereto, according to the fourth aspect of the invention described above, when the zigzag structure is deformed to bend, the first elastic member and the second elastic member, which are made of rubber and which are individually fixed firmly attached to a pair of leg portions on both sides of the inter-leg-portion elastic member, are in contact with each other when compressed, thus minimizing the possibility of the occurrence of slide friction between the first elastic member and the second elastic member.

Thus, the bending deformation of the zigzag structure can be smoothly accomplished and the elastic force generated in the zigzag structure, i.e. the elastic force acting to cancel the bending deformation of the zigzag structure, can be smoothly increased as the bending degree of the zigzag structure increases.

Further, in the third aspect or the fourth aspect of the invention described above, the inter-leg-portion elastic member is provided between a pair of leg portions that extends in a bifurcated manner from each of a plurality of top portions positioned on one side in the amplitude direction of the zigzag structure, and the stiffness or the arrangement of the inter-leg-portion elastic member corresponding to each of the plurality of top portions may be set such that, upon bending deformation of the zigzag structure such that one side in the amplitude direction thereof is placed on an outer side and the other side thereof is placed on the inner side, the strain of the inter-leg-portion elastic member corresponding to each of the plurality of top portions positioned on one side in the amplitude direction of the zigzag structure approximates to uniformity with each other (a fifth aspect of the invention).

According to the fifth aspect of the invention, when the zigzag structure is deformed to bend such that one side in the amplitude direction of the zigzag structure is placed on the outer side and the other side thereof is placed on the inner side, the strain developed in each inter-leg-portion elastic member is mutually uniform, making it possible to prevent undue strain from occurring in any one inter-leg-portion elastic member, as compared with other inter-leg-portion elastic members. This permits prolonged lives of the inter-leg-portion elastic members. Further, variations in the lives of the inter-leg-portion elastic members can be prevented.

Further, in the second aspect to the fourth aspect of the invention, a stopper member which prevents the interval of the pair of leg portions, which extends in the bifurcated manner from each top portion, from becoming smaller than a predetermined amount may be fixedly installed to at least one of the pair of leg portions for each top portion positioned on one side in the amplitude direction of the zigzag structure (a sixth aspect of the invention).

If the bending degree of the zigzag structure reaches an excessive level, then the zigzag structure tends to develop a deformation that causes the zigzag structure to bend in a direction about the axis in the amplitude direction thereof (hereinafter, the deformation will be referred to as the abnormal bending deformation in some cases).

On the other hand, according to the sixth aspect of the invention, the stopper member prevents the interval of the pair of leg portions, which extends in the bifurcated manner from each top portion positioned on one side in the amplitude direction of the zigzag structure, from becoming smaller than the predetermined amount, thus preventing the bending degree of the zigzag structure from becoming excessive. As a result, the occurrence of the abnormal bending deformation of the zigzag structure can be prevented.

Further, in the sixth aspect of the invention, a configuration may be adopted, in which the stopper members are fixedly installed to both of the pair of leg portions, which extends in the bifurcated manner from each top portion positioned on one side in the amplitude direction of the zigzag structure, and the stopper members come in contact with each other when the interval between the pair of leg portions reduces to the predetermined amount. Alternatively, a configuration may be adopted, in which the stopper member is fixedly installed to one of the foregoing pair of leg portions and the stopper member comes in contact with the other leg when the interval between the pair of leg portions reduces to the predetermined amount.

In the configuration in which the stopper members come in contact with each other, the contact pressure of the stopper members blocks the zigzag structure from bending about the axis in the amplitude direction thereof. Further, in the configuration in which the stopper member comes in contact with the leg portion, the contact pressure between the stopper member and the leg portion blocks the zigzag structure from bending about the axis in the amplitude direction thereof. Thus, the effect for preventing the zigzag structure from developing the abnormal bending deformation can be enhanced.

In the sixth aspect of the invention, the stopper member corresponding to each top portion positioned on one side in the amplitude direction of the zigzag structure may be composed of a pair of stopper members fixedly installed, opposing the pair of leg portions extending in the bifurcated manner from the top portion, and the pair of stopper members may come in contact with each other and a recession formed in one of the pair of stoppers and a projection formed on the other thereof may fit each other in the case where the interval between the pair of leg portions on both sides thereof reduces to a predetermined amount (a seventh aspect of the invention).

According to the seventh aspect of the invention, if the interval of the pair of leg portions, which extends in the bifurcated manner from each top portion positioned on one side in the amplitude direction of the zigzag structure, reduces to the predetermined amount, then the pair of stopper members between the pair of leg portions come in contact with each other thereby to block the interval between the pair of leg portions from reducing to less than the predetermined amount.

At the same time, the recession formed in one of the pair of stopper members and the projection formed on the other thereof fit each other, so that the mutual attitude relationship between the pair of leg portions is restricted by the fitting. This makes it possible to further effectively prevent the occurrence of the abnormal deformation of the zigzag structure.

The section of the zigzag structure that is constituted of each top portion and the pair of leg portions extending in the bifurcated manner from the top portions may adopt a variety of shapes. The shapes may include, for example, one with a sharp or pointed top portion, one with a curved top portion, or one with a flat top portion.

As a more specific example, the zigzag structure may adopt, for example, the following form. The zigzag structure employs a structure constituted by connecting a plurality of element members, each of which is composed of a plate-like elastic member having a width in a direction orthogonal to the amplitude direction of the zigzag structure and the direction of an amplitude centerline, and which is formed into a U shape having a single top portion and a pair of leg portions integrally extending in a bifurcated manner from the top portion, the plurality of element members are placed such that the top portions thereof are arranged in the direction of the amplitude centerline as the top portions positioned on one side in the amplitude direction of the zigzag structure, and further, in the case where one of the element members that are adjacent to each other is denoted as a first element member and the other thereof is denoted as a second element member, a distal end of a first A leg portion, which is the leg portion of a pair of leg portions of the first element member that is on the second element member side, and a distal end of a second A leg portion, which is the leg portion of a pair of leg portions of the second element member on the first element member side are connected into one piece, and a portion connecting the distal end of the first A leg portion and the distal end of the second A leg portion provides each top portion positioned on the other side in the amplitude direction of the zigzag structure.

The top portion of each of the foregoing element members may have either a curved shape or a flat shape.

If the zigzag structure is configured as the structure formed by connecting the plurality of U-shaped element members as described above, then the zigzag structure is preferably configured such that the first A leg of the first element member and the second A leg of the second element member come in contact with each other in a state wherein a tension of a predetermined value or more is applied to the flexible lengthy member by the tension application unit in the second to the seventh aspects of the invention (an eighth aspect of the invention).

According to the eighth aspect of the invention, the first A leg of the first element member and the second A leg of the second element member come in contact with each other in a state wherein a tension of a predetermined value or more is applied to the flexible lengthy member by the tension application unit. This firmly restricts the pitch of the top portions (the interval between top portions adjacent to each other in the direction of the amplitude centerline) positioned on one side (on the flexible lengthy member side) in the amplitude direction of the zigzag structure.

With this arrangement, when the zigzag structure is deformed to bend such that one side in the amplitude direction of the zigzag structure is placed on the outer side and the other side is placed on the inner side, the stability, i.e. repeatability, of the relationship between the bending degree and an elastic force generated in the zigzag structure (an elastic force acting to cancel the bending deformation of the zigzag structure) can be enhanced.

Further, the mutual contact between the first A leg of the first element member and the second A leg of the second element member minimizes the possibility of the occurrence of a twist of the first A leg of the first element member and the second A leg of the second element member. This leads to higher stiffness in the direction about the axis in the amplitude direction of the zigzag structure and a minimized possibility of the occurrence of the abnormal bending deformation of the zigzag structure.

Preferably, the first to the eighth aspects of the invention described above further include a cover member that has a pair of cover surfaces disposed to cover both side surfaces of the zigzag structure in the direction of the thickness of the zigzag structure, which is the direction orthogonal to the amplitude direction of the zigzag structure and the direction of an amplitude centerline, with an interval provided between the pair of cover surfaces in the direction of the thickness, and the deformation of the zigzag structure is restricted to a deformation within the interval of the pair of cover surfaces of the cover member (a ninth aspect of the invention).

According to the ninth aspect of the invention, the occurrence of the abnormal bending deformation of the zigzag structure can be effectively prevented by the cover member.

In the ninth aspect of the invention, the cover member is preferably configured to bend as the zigzag structure is deformed to bend within the interval of the pair of cover surfaces of the cover member (a tenth aspect of the invention).

According to the tenth aspect of the invention, the cover member can be bent according to the bending deformation of the zigzag structure, thus making it possible to control the size (especially the area of the cover member observed from the direction of the thickness of the zigzag structure) of the cover member to a necessary minimum.

Further, the joint mechanism in accordance with the present invention may be configured as described below. The joint mechanism in accordance with the present invention is a joint mechanism connecting a first member and a second member in a relatively displaceable manner, including:

a zigzag structure which is configured to be arranged in a row between the first member and the second member in a zigzag pattern from the first member toward the second member, having an amplitude in a lateral direction, an end portion thereof adjacent to the first member and an end portion thereof adjacent to the second member being connected to the first member and the second member, respectively, and which is configured to be deformable such that the length in the direction of an amplitude centerline of the zigzag structure and the bending degree of the amplitude centerline can be changed by a pair of leg portions, which extends in a bifurcated manner from each top portion positioned on each of both sides in an amplitude direction of the zigzag structure, and which are relatively rotatably connected about an axis of a support shaft through the intermediary of the support shaft, which has the axis orthogonal to the amplitude direction of the zigzag structure and the direction of the amplitude centerline and which is provided on the top portion;

an inter-leg-portion elastic member which is provided between a pair of leg portions extending in a bifurcated manner from each top portion positioned on each of both sides in the amplitude direction of the zigzag structure and which is composed of an elastic member which is compressed and generates an elastic force as an interval of the pair of leg portions decreases;

a flexible lengthy member which is disposed to extend from the first member toward the second member, which has one end portion adjacent to the first member fixed to the first member, which is provided to be travelable with respect to the second member, and which applies, to the zigzag structure, a force for pressing the zigzag structure between the first member and the second member in a state in which a tension is being applied; and a tension application unit which applies a tension to the flexible lengthy member from the other end portion side of the flexible lengthy member and which is configured to be capable of changing the magnitude of the tension (an eleventh aspect of the invention).

According to the eleventh aspect of the invention, the magnitude of the tension to be applied to the flexible lengthy member can be adjusted by the tension application unit.

In this case, if the tension applied to the flexible lengthy member is zero or small, then the pair of leg portions extending in the bifurcated manner from each top portion positioned on each of both sides in the amplitude direction of the zigzag structure are allowed to relatively rotate about the axis of the support shaft provided on the top portion without being restrained (or being hardly restrained).

Hence, the length in the direction of the amplitude centerline of the zigzag structure or the bending degree of the amplitude centerline can be changed in a relatively wide range while maintaining a state in which the inter-leg-portion elastic member provided between the pair of leg portions extending from each top portion is not compressed much.

In this situation, therefore, the relative displacement between the first member and the second member can be accomplished while controlling the elastic force generated by the zigzag structure between the first member and the second member to a small value, including zero.

Meanwhile, if the tension applied to the flexible lengthy member is increased to a certain extent, then the first member is pressed against the second member through the intermediary of the zigzag structure and the interval between the pair of leg portions extending from each top portion of the zigzag structure is reduced, thus compressing the inter-leg-portion elastic member between the pair of leg portions. As a result, an elastic force that prevents the relative rotation of the pair of leg portions is generated, restricting the deformation of the zigzag structure. In particular, the length of the zigzag structure in the direction along the flexible lengthy member is restricted, making it difficult for the zigzag structure to develop a deformation that increases the length.

In this situation, if the first member and the second member are relatively displaced to bend the zigzag structure (more specifically, to bend the zigzag structure such that one side in the amplitude direction of the zigzag structure is placed on the outer side, while the other side thereof is placed on the inner side), then the inter-leg-portion elastic member between the pair of leg portions extending from each top portion positioned on the other side is further compressed, causing the zigzag structure to promptly generate an elastic force that functions to cancel the bending of the zigzag structure. Further, the elastic force increases with high responsiveness as the bending degree (the bending degree of the amplitude centerline) of the zigzag structure increases.

Accordingly, in the case where the first member and the second member are relatively displaced to bend the zigzag structure by increasing the tension applied to the flexible lengthy member, a force (moment) acting to cancel the bending of the zigzag structure can be generated between the first member and the second member by the elastic force of the zigzag structure.

Further, the bending of the zigzag structure is not the bending about a fixed axis, so that the zigzag structure can be smoothly bent according to the relative displacement of the first member and the second member regardless of whether the relative displacement of the first member and the second member for causing the zigzag structure to bend is the rotational displacement about a single axis.

Thus, the joint mechanism according to the eleventh aspect of the invention makes it possible to generate power for the bending as necessary by the structure featuring a high degree of freedom of bending, as with the first aspect of the invention.

In the eleventh aspect of the invention, preferably, the inter-leg-portion elastic member is constituted of a first elastic member made of rubber that is firmly fixed to one leg portion of the pair of leg portions on both sides of the inter-leg-portion elastic member and a second elastic member made of rubber that is firmly fixed to the other leg portion so as to oppose the first elastic member, and the first elastic member and the second elastic member are compressed in a state of being in contact with each other when compressed between the pair of leg portions (a twelfth aspect of the invention).

In the foregoing eleventh aspect of the invention, when, for example, the zigzag structure is deformed to bend with the rubber inter-leg-portion elastic member firmly fixed to one of the pair of leg portions on both sides thereof (more specifically, if the zigzag structure is deformed to bend such that one side in the amplitude direction thereof is placed on the outer side and the other side is placed on the inner side), the inter-leg-portion elastic member can be pressed against the other leg portion of the pair of leg portions on both sides thereof so as to compress the inter-leg-portion elastic member.

In such a case, however, when the zigzag structure is deformed to bend, a slide friction tends to occur between the inter-leg-portion elastic member and the leg portions against which the inter-leg-portion elastic member is pressed, thus easily interfering with smooth bending deformation of the zigzag structure.

In contrast thereto, according to the twelfth aspect of the invention described above, when the zigzag structure is deformed to bend, the first elastic member and the second elastic member, which are made of rubber and which are individually fixed firmly to a pair of leg portions on both sides of the inter-leg-portion elastic member, come in contact with each other and are compressed, thus minimizing the possibility of the occurrence of the slide friction between the first elastic member and the second elastic member, as with the fourth aspect of the invention.

Thus, the bending deformation of the zigzag structure can be smoothly accomplished and the elastic force generated in the zigzag structure, i.e. the elastic force acting to cancel the bending deformation of the zigzag structure, can be smoothly increased as the bending degree increases.

Further, in the eleventh or the twelfth aspect of the invention, as the arrangement configuration of the flexible lengthy member, the following arrangement configuration may be adopted. The flexible lengthy member is disposed, for example, to extend at a position adjacent to one side of both sides in the amplitude direction of the zigzag structure (a thirteenth aspect of the invention).

According to the thirteenth aspect of the invention, if the zigzag structure is deformed to bend such that one side of both sides in the amplitude direction, which one side is adjacent to the flexible lengthy member, is placed on the outer side and the other side in the amplitude direction is placed on the inner side in a state wherein the tension applied to the flexible lengthy member is relatively high, then an elastic force of a magnitude in a wide range that functions to cancel the bending deformation can be efficiently generated in the zigzag structure.

In the thirteenth aspect of the invention, regarding the inter-leg-portion elastic member provided between a pair of leg portions extending in a bifurcated manner from each top portion positioned on one side in the amplitude direction of the zigzag structure, the stiffness or the arrangement of the inter-leg-portion elastic member corresponding to each top portion may be set such that, in the case where the zigzag structure is deformed to bend such that one side in the amplitude direction thereof is placed on the outer side and the other side thereof is placed on the inner side, the strain of the inter-leg-portion elastic member corresponding to each top portion positioned on one side in the amplitude direction of the zigzag structure approximates to uniformity with each other (a fourteenth aspect of the invention).

According to the fourteenth aspect of the invention, when the zigzag structure is deformed to bend such that one side in the amplitude direction of the zigzag structure is placed on the outer side and the other side thereof is placed on the inner side, the strain developed in each inter-leg-portion elastic member is mutually uniform, making it possible to prevent undue strain from occurring in any one inter-leg-portion elastic member, as compared with other inter-leg-portion elastic members. This permits prolonged lives of the inter-leg-portion elastic members. Further, variations in the lives of the inter-leg-portion elastic members can be prevented.

The joint mechanisms according to the first to the tenth aspects of the invention described above can be used in, for example, the following form. The first member and the second member can be used as the members attached to a crus or a foot of a leg of a person and a thigh or waist of the person, respectively, in a state in which the zigzag structure is positioned on the side of a knee joint of the leg of the person (a fifteenth aspect of the invention). The same applies to the joint mechanisms in the eleventh to the fourteenth aspects of the invention (a sixteenth aspect of the invention).

According to the fifteenth or the sixteenth aspect of the invention, if the leg of the person is bent, i.e. the knee is bent, or the leg is vertically moved relative to the waist in a state in which a relatively high tension is being applied to the flexible lengthy member by the tension application unit, then an elastic force that functions to stretch the leg of the person is generated between the crus or the foot of the leg and the thigh or the waist.

This arrangement makes it easy for a person with weak legs to support his or her upper body when, for example, squatting or standing up from a squat, or sitting on a chair or standing up from the chair.

Further, in the first to the tenth aspects of the invention or the fifteenth aspect of the invention, the tension application unit may adopt a configuration that includes an actuator which generates a driving force for applying the tension to the flexible lengthy member, and a brake unit which is provided in a power transmission system between the actuator and the flexible lengthy member and which is capable of operating in a state in which a travel motion of the flexible lengthy member is braked and a state in which the braking is cleared (a seventeenth aspect of the invention). The same applies to the eleventh to the fourteenth aspects of the invention or the sixteenth aspect of the invention (an eighteenth aspect of the invention).

The tension application unit can be configured to apply a tension to the flexible lengthy member by, for example, the driving force of an actuator. If, however, the actuator is operated on a steady basis to apply a relatively high tension to the flexible lengthy member, then the actuator tends to consume a large amount of energy.

In contrast thereto, according to the seventeenth or the eighteenth aspect of the invention, a state in which a tension is being applied to the flexible lengthy member can be maintained without the need for the driving force of the actuator by, for example, setting the brake unit to the state for braking the travel motion of the flexible lengthy member after the tension is applied to the flexible lengthy member by the driving force of the actuator.

Thus, the load on the actuator can be reduced and the energy consumption of the actuator can be also reduced.

Further, in the first to the tenth aspects of the invention or the fifteenth aspect of the invention, the tension application unit may adopt a configuration including an actuator which generates a driving force for applying the tension to the flexible lengthy member and a clutch unit which is capable of operating in a state in which the transmission of power between the actuator and the flexible lengthy member is cut off and a state in which the transmission of power is carried out (a nineteenth aspect of the invention). The same applies to the eleventh to the fourteenth aspects of the invention or the sixteenth aspect of the invention (a twentieth aspect of the invention).

In the case where the tension application unit is configured to apply a tension to the flexible lengthy member by, for example, the driving force of the actuator, if a state in which the power can be transmitted between the actuator and the flexible lengthy member is maintained after the application of the tension by the actuator is cleared, then a movable part of the actuator (e.g. a rotor of an electric motor) becomes a load as the flexible lengthy member travels when the first member starts to be relatively displaced with respect to the second member, so that a resistance force from the relative displacement of the first member with respect to the second member tends to be generated.

In contrast thereto, according to the nineteenth aspect of the invention or the twentieth aspect of the invention, the power transmission between the actuator and the flexible lengthy member is cut off in the state wherein the application of the tension by the actuator has been cleared, thereby blocking the movable part of the actuator from moving as the flexible lengthy member travels.

Hence, in the state wherein the application of the tension by the actuator has been cleared, the resistance force of the relative displacement of the first member with respect to the second member can be reduced.

Further, in the seventeenth aspect of the invention, the eighteenth aspect of the invention, the nineteenth aspect of the invention, or the twentieth aspect of the invention, the tension application unit may adopt a configuration further including a pre-tension generating unit which applies a pre-tension, which is an anti-slack tension for preventing a slack of the flexible lengthy member, to the flexible lengthy member (a twenty-first aspect of the invention, a twenty-second aspect of the invention, a twenty-third aspect of the invention, and a twenty-fourth aspect of the invention).

The term "pre-tension" is usually used in relation to the retracting function of a vehicle seat belt. In the present description, however, the term "pre-tension" is used to mean the anti-slack tension applied to the flexible lengthy member to prevent the flexible lengthy member from slacking, as described above.

According the twenty-first aspect of the invention, the twenty-second aspect of the invention, the twenty-third aspect of the invention, or the twenty-fourth aspect of the invention, the occurrence of the slack of the flexible lengthy member can be prevented by the pre-tension generating unit in the case where the flexible lengthy member slacks or is likely to slack, regardless of whether the tension is being applied to the flexible lengthy member by the actuator or the brake unit.

Further, the twenty-first aspect of the invention, the twenty-second aspect of the invention, the twenty-third aspect of the invention, or the twenty-fourth aspect of the invention described above may adopt a configuration further including a one-way clutch mechanism which is provided between the actuator and the flexible lengthy member and which blocks the transmission of a force in a direction in which the flexible lengthy member slacks (a twenty-fifth aspect of the invention, the twenty-sixth aspect of the invention, the twenty-seventh aspect of the invention, and a twenty-eighth aspect of the invention).

According to the twenty-fifth aspect of the invention, the twenty-sixth aspect of the invention, the twenty-seventh aspect of the invention, or a twenty-eighth aspect of the invention, the prevention of the occurrence of the slack of the flexible lengthy member by the pre-tension generating unit makes it possible to prevent a friction force generated at the actuator or a friction force generated at the power transmission mechanism, such as a reduction gear, between the actuator and the one-way clutch mechanism from acting on the flexible lengthy member. Thus, the effect for preventing the occurrence of the slack of the flexible lengthy member can be further enhanced by the pre-tension generating unit.

Further, in the first to the tenth aspects of the invention or the fifteenth aspect of the invention, the tension application unit may adopt a configuration including a locking mechanism capable of switching between a lock state in which the flexible lengthy member is locked so as to block the flexible lengthy member from traveling with respect to the second member in a direction in which the first member moves away from the second member and an unlock state in which the locking is cleared; and a pre-tension generating unit which applies a pre-tension, which is an anti-slack tension for preventing the slack of the flexible lengthy member, to the flexible lengthy member (a twenty-ninth aspect of the invention). The same applies to the eleventh to the fourteenth aspects of the invention or the sixteenth aspect of the invention (a thirtieth aspect of the invention).

According to the twenty-ninth aspect of the invention or the thirtieth aspect of the invention, setting the locking mechanism in the lock state causes the flexible lengthy member to restrict the distance between the first member and the second member in a direction along the flexible lengthy member. This makes it possible to apply a tension that is higher than the pre-tension to the flexible lengthy member when the zigzag structure is bent to increase the distance.

Meanwhile, if the locking mechanism is set to the unlock state, then the tension applied to the flexible lengthy member can be controlled to a very small level approximately equal to the pre-tension.

Hence, the magnitude of the tension applied to the flexible lengthy member can be changed also according to the twenty-ninth aspect of the invention or the thirtieth aspect of the invention. Further, in the twenty-ninth aspect of the invention or the thirtieth aspect of the invention, the locking mechanism may adopt a configuration in which the flexible lengthy member is mechanically locked by recession and projection fitting or the like, thus permitting a smaller design that does not require a large driving force.

DESCRIPTION OF THE PREFERRED EMBODIMENTS

First Embodiment

A first embodiment of the joint mechanism in accordance with the present invention will be described below with reference to FIG. 1 to FIG. 7.

The joint mechanism of the present embodiment is a joint mechanism used for a walking assist device for assisting a person with his or her walking motion and the like.

Figure 1:
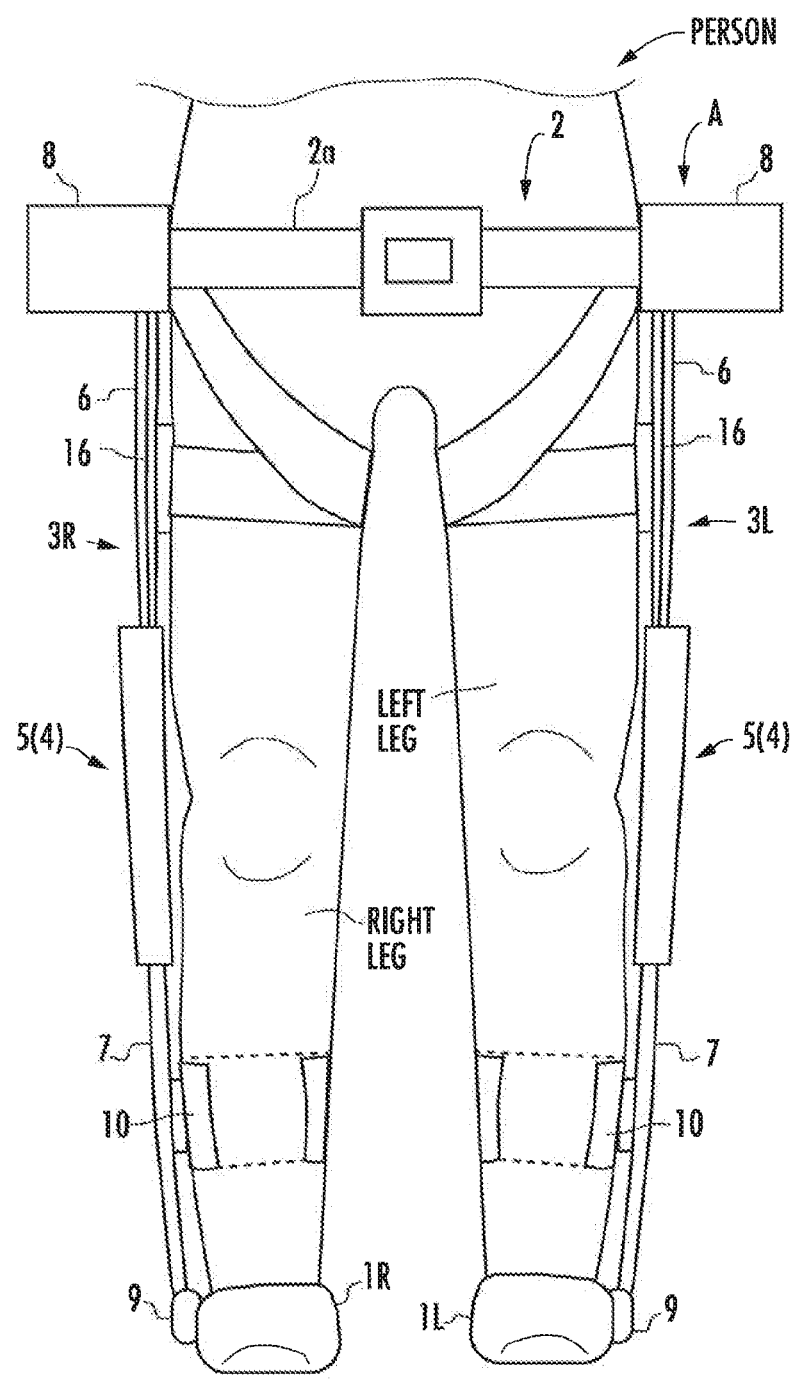
FIG. 1 is a diagram illustrating the configuration of a walking assist device provided with a joint mechanism of an embodiment according to the present invention.

FIG. 1 illustrates a schematic configuration of the walking assist device. As illustrated, a walking assist device A has foot-worn portions 1L, 1R attached to left and right feet, respectively, of a person, a waist-worn portion 2 attached to the waist of the person and the neighborhood thereof, and legs 3L, 3R disposed to extend along and on the outer sides of the left and right legs of the person. Each of the legs 3L, 3R incorporates a main body 5 of a joint mechanism 4 (hereinafter referred to as "the joint mechanism main body 5").

The suffixes L and R as in the foot-worn portions 1L, 1R are used as the reference characters denoting members on the left side and the right side, respectively, of a person wearing the walking assist device A. In the following description, however, the suffixes L and R may be omitted if there is no need to distinguish left and right.

Each of the foot-worn portions 1 has a shoe-like shape and is attached to a foot by the foot being placed therein.

The waist-worn portion 2 has a harness structure in the present embodiment. The waist-worn portion 2 is constituted mainly of a waist belt 2a wound around the waist of the person, leg belts 2b, 2b wound around the bases of the left and right legs of the person, and connecting belts 2c, 2c that connect the leg belts 2b, 2b to the waist belt 2a.

Each of the legs 3 has the joint mechanism main body 5 disposed on the side of a knee joint of the leg of the person, and a rod-shaped upper frame 6 and a rod-shaped lower frame 7 extended upward and downward, respectively, from the joint mechanism main body 5.

The joint mechanism main body 5 is a section that has a first member, a second member, and a zigzag structure, which will be discussed hereinafter. Each of the legs 3 can be bent and stretched at the joint mechanism main body 5. In FIG. 1, for the convenience of illustration, the actual construction of the joint mechanism main body 5 is omitted, and the joint mechanism main body 5 is schematically illustrated by a square shape.

The upper end portion of each of the upper frames 6 is inserted in a chassis 8 fixed to the side surface of the waist belt 2a of the waist-worn portion 2 on the same side of the leg 3 (the left side or the right side). Further, the upper frame 6 is swingably connected to the waist belt 2a through a joint mechanism composed of a free joint or the like (not illustrated) in the chassis 8. The chassis 8 is a chassis that houses a tension application unit and the like, which will be discussed hereinafter.

Further, the upper frame 6 is fixed to the outer side surface of the leg belt 2b (the leg belt 2b on the same side as the leg 3) of the waist-worn portion 2. Thus, when the leg of the person on the same side as the leg 3 is moved, the upper frame 6 moves integrally with the thigh of the leg.

The lower end portion of the lower frame 7 is swingably connected to the foot-worn portion 1 (the foot-worn portion 1 on the same side as the leg 3) through a joint mechanism 9 composed of a free joint or the like. Further, the lower frame 7 is fixed to a semi-cylindrical crus-worn portion 10 attached to hold the crus on the back side of the crus of the leg of the person on the same side as the leg 3. Hence, when the leg of the person on the same side as the leg 3 is moved, the lower frame 7 moves integrally with the crus of the leg.

The joint mechanism of the upper end portion of the upper frame 6 or the joint mechanism 9 of the lower end portion of the lower frame 7 may be a joint mechanism having a one-axis or two-axis joint.

The configuration of the joint mechanism main body 5 will now be described in detail with reference to FIG. 2 to FIG. 5.

The joint mechanism main body 5 of each of the legs 3 has a first member 11 and a second member 12, and a zigzag structure 13 that relatively displaceably connects the first member 11 and the second member 12, as illustrated in FIG. 2 to FIG. 5. Further, the first member 11, the second member 12, and the zigzag structure 13 are covered by a cover member 20.

Figure 2:
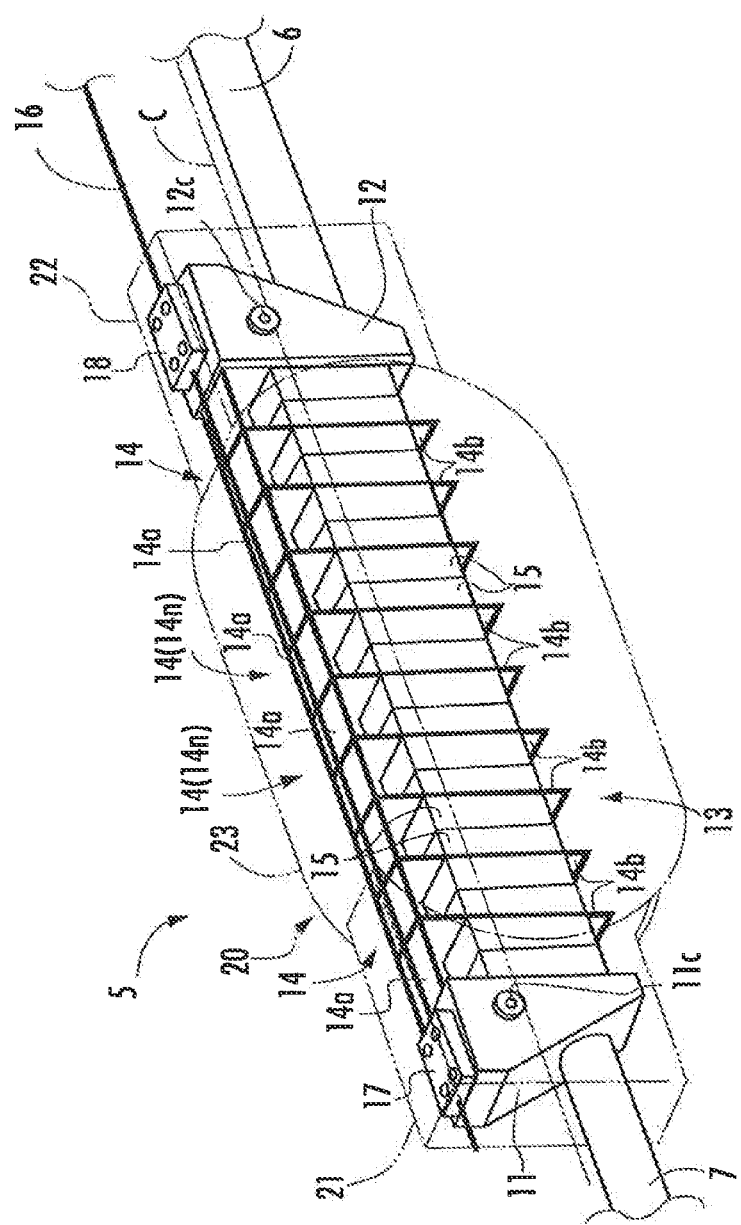
FIG. 2 is a perspective view illustrating the configuration of an essential section of a main body of the joint mechanism of a first embodiment.
Figure 3:
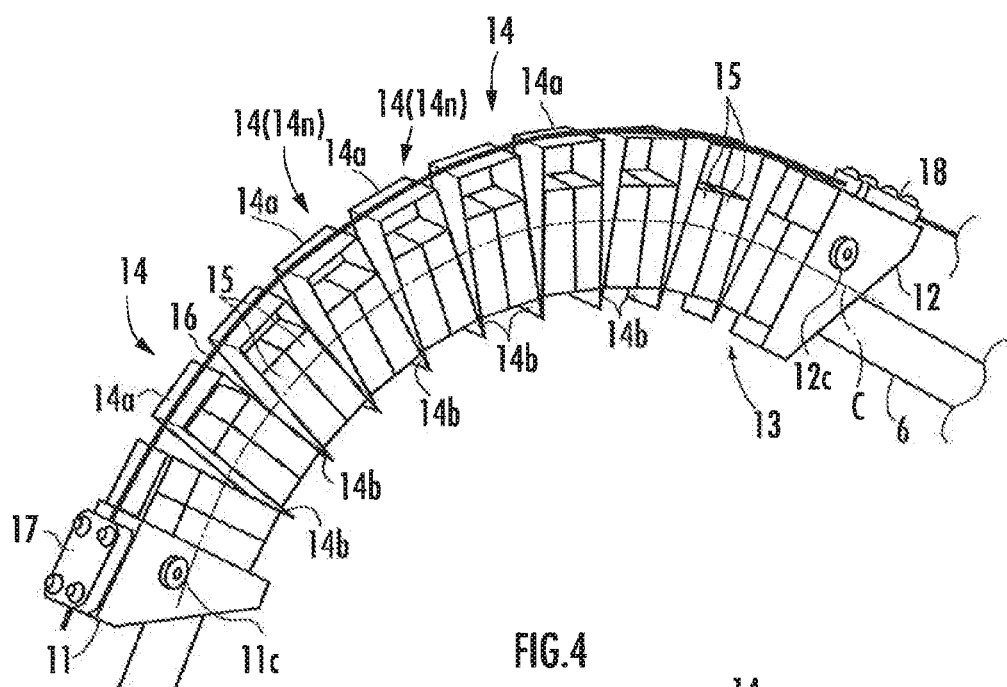
FIG. 3 is another perspective view illustrating the configuration of the essential section of the main body of the joint mechanism of the first embodiment.
Figure 4:
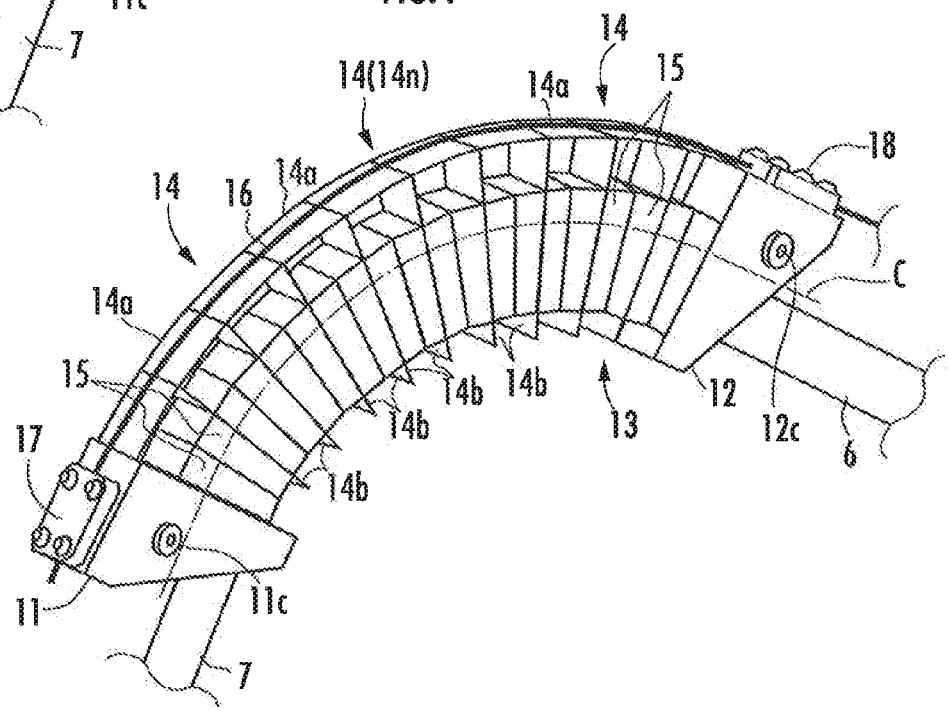
FIG. 4 is yet another perspective view illustrating the configuration of the essential section of the main body of the joint mechanism of the first embodiment.
Figure 5:
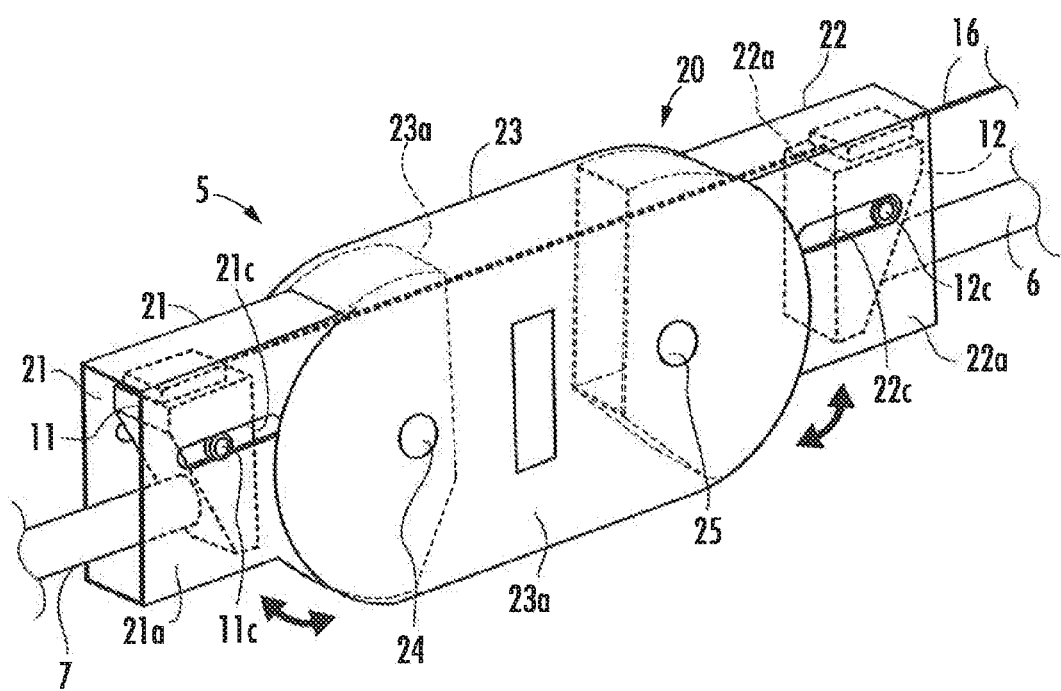
FIG. 5 is a perspective view illustrating a cover member provided on the main body of the joint mechanism of the first embodiment.

The cover member 20 is indicated by the two-dot chain line in FIG. 2, and the cover member 20 is not illustrated in FIG. 3 and FIG. 4. In FIG. 5, the zigzag structure 13 is not illustrated.

Referring to FIG. 2 to FIG. 4, the first member 11 and the second member 12 are highly rigid members made of a metal or a resin. The lower frame 7 is extended from the first member 11. Further, the upper frame 6 is extended from the second member 12. Thus, the first member 11 is attached to the crus through the lower frame 7 such that the first member 11 moves integrally with the crus of the leg of the person. Further, the second member 12 is attached to the thigh through the upper frame 6 such that the second member 12 moves integrally with the thigh of the leg of the person.

The zigzag structure 13 is a structure extending in a zigzag manner from the first member 11 toward the second member 12. The zigzag structure 13 in the present embodiment is constructed of a plurality of element members 14, which are arranged in a row and connected. Each of the element members 14 is formed of a metallic plate-like elastic member in a bent shape. Each of the element members 14 has a top portion 14a and a pair of leg portions 14b, 14b extending in a bifurcated manner from the top portion 14a, the top portion 14a and the pair of leg portions 14b, 14b being integrally formed.

In the present embodiment, the top portion 14a is formed like a flat plate. Further, the pair of leg portions 14b, 14b extends from both side edges of the top portion 14a such that the leg portions 14b, 14b stand relative to the top portion 14a.

Accordingly, each of the element members 14 is approximately formed into a U shape (U shape with the bottom portion of the U on the upper side in FIG. 2 to FIG. 4). In this case, the portion corresponding to the bottom portion of the U shape, i.e. the top portion 14a, of each of the element members 14 is formed to be flat. In other words, therefore, each of the element members 14 is formed in the U shape with the flat bottom portion.

The element members 14 configured as described above are capable of elastically deforming such that the leg portions 14b swing relative to the top portion 14a, i.e. such that the standing angles of the leg portions 14b relative to the top portions 14a change.

According to the present embodiment, in a natural state, in which there is no elastic deformation of the element members 14 (a state in which there is no stress), each of the leg portions 14b stands in a direction substantially perpendicular to the top portion 14a. Alternatively, however, each of the leg portions 14b may extend from the top portion 14a in a direction aslant relative to the perpendicular direction in the natural state of the element members 14.

The plurality of element members 14 constituting the zigzag structure 13 are arranged to be aligned in the direction of the intervals of the pairs of the leg portions 14b, 14b. Further, the distal portions of the adjacent leg portions 14b, 14b of the adjacent element members 14, 14 are connected into one piece by welding or bonding.

More specifically, if one of any adjacent element members 14, 14 of the zigzag structure 13 is denoted by a first element member 14m and the other is denoted by a second element member 14n, then the distal portion of the leg portion 14b of the first element member 14m on the second element member 14n side (corresponding to the first A leg portion in the present invention) and the distal portion of the leg portion 14b of the second element member 14n on the first element member 14m side (corresponding to the second A leg portion in the present invention) are connected into one piece by, for example, welding or bonding.

Thus, the zigzag structure 13 is configured to extend in the zigzag pattern with an amplitude in the lateral direction (in the vertical direction in FIG. 2) from the first member 11 toward the second member 12, as illustrated in FIG. 2 to FIG. 4.

In this case, the top portion 14a of each of the element members 14 is the top portion (the turnback portion) of one side (the upper side in FIG. 2) of both sides (the upper side and the lower side in FIG. 2) in the amplitude direction of the zigzag structure 13. Further, the connected portion (the distal portion) of the adjacent leg portions 14b, 14b of the adjacent element members 14, 14 (14m, 14n) is the top portion (the turnback portion) of the other side (the lower side in FIG. 2) in the amplitude direction of the zigzag structure 13.

Both end portions (both end portions in the direction of an amplitude centerline C illustrated in FIG. 2 to FIG. 4) of the zigzag structure 13 configured as described above are connected to the first member 11 and the second member 12, respectively. More specifically, the leg portion 14b of the element member 14 of the zigzag structure 13 that is positioned closest to the first member 11, i.e. the leg portion 14b on the first member 11 side, is firmly fixed to the first member 11 by welding, bonding or the like.

Further, the leg portion 14b of the element member 14 of the zigzag structure 13 that is positioned closest to the second member 12, i.e. the leg portion 14b on the second member 12 side is firmly fixed to the second member 12 by welding, bonding or the like.

The amplitude centerline C means the line that extends from the first member 11 toward the second member 12 at the central position or substantially the central position of the width of the zigzag structure 13 in the amplitude direction of the zigzag structure 13.

In the zigzag structure 13 configured as described above, each of the element members 14 elastically deforms such that the leg portions 14b of each of the element members 14 swing relative to the top portion 14a in response to an external force, thus making it possible to change one or both of the pitch of the top portion on one side in the amplitude direction of the zigzag structure 13, i.e. the interval between the top portions that are adjacent in the direction of the amplitude centerline C, and the pitch of the top portion on the other side.

The arrangement enables the zigzag structure 13 to expand or contact so as to change the length of the zigzag structure 13 in the direction of the amplitude centerline C or enables the zigzag structure 13 to bend so as to change the bending degree of the amplitude centerline C.

FIG. 2 illustrates the zigzag structure 13, which has been contracted in the direction of the amplitude centerline C, and the amplitude centerline C has become substantially straight. Further, FIG. 3 illustrates the zigzag structure 13, which has expanded in the direction of the amplitude centerline C and which is in a bent state, and FIG. 4 illustrates the zigzag structure 13, which has contracted in the direction of the amplitude centerline C and which is in a bent state.

Supplementarily, the top portion 14a itself of each of the element members 14 may be difficult to be elastically deformed. In other words, the top portions 14a of the element members 14 may have higher stiffness than the remaining portions. For example, the stiffness of the top portions 14a may be enhanced by firmly attaching hard foamed resins or the like to the top portions 14a.

The zigzag structure 13 of the present embodiment is further provided with a plurality of elastic members 15 composed of elastic members that are separate from the element members 14.

Specifically, as illustrated in FIG. 2 to FIG. 4, the elastic members 15, 15 made of rubber, which are firmly attached to the mutually opposing surfaces of the pair of the leg portions 14b, 14b, are provided facing each other between the pair of the leg portions 14b, 14b of each of the element members 14 of the zigzag structure 13. Each of the elastic members 15 is formed like, for example, an approximately rectangular parallelepiped. Hereinafter, the elastic members 15 will be referred to as the inter-leg-portion elastic members 15. The inter-leg-portion elastic members 15, 15 between the pair of leg portions 14b, 14b correspond to the first elastic member and the second elastic member in the present invention.

The thickness of each of the inter-leg-portion elastic members 15, 15 between the pair of the leg portions 14b, 14b of each of the element members 14 is set such that the inter-leg-portion elastic members 15, 15 are pressed against each other to generate an elastic force in the direction for increasing the interval between the pair of the leg portions 14b, 14b when the element members 14 are elastically deformed to decrease the interval between the pair of the leg portions 14b, 14b.

Accordingly, in the zigzag structure 13 of the present embodiment, if the element member 14 is elastically deformed to decrease the interval between the pair of the leg portions 14b, 14b of each of the element members 14, then an elastic force in the direction for cancelling the elastic deformation of the element members 14 is produced by the element member 14 itself and the inter-leg-portion elastic members 15, 15 between the leg portions 14b, 14b of the element member 14.

Further, a flexible lengthy member 16 is extended from the first member 11. The flexible lengthy member 16 may use, for example, a wire or a belt. The flexible lengthy member 16 in the present embodiment is formed of a wire. Hereinafter, the flexible lengthy member 16 will be referred to as the wire 16.

The wire 16 is disposed to extend in substantially the same direction as the direction of the amplitude centerline C from the first member 11 side toward the second member 12, i.e. to extend along the row of the top portions 14a of the element members 14, on the outer side of the top portions 14a of the element members 14 as the top portions on one side in the amplitude direction of the zigzag structure 13.

Further, the end of the wire 16 adjacent to the first member 11 is fixed to the first member 11 through a wire fixing member 17 in which the end of the wire 16 is inserted. The portion of the wire 16 that opposes the second member 12 is slidably inserted in a wire insertion member 18 firmly attached to the second member 12. Thus, the wire 16 is travelable with respect to the second member 12.

Further, the wire 16 is extended from the location of the second member 12 toward the chassis 8 (the chassis 8 on the same side (the left or right side) as the leg 3 having the zigzag structure 13) (refer to FIG. 1), and connected to a tension application unit 30, which will be discussed hereinafter, in the chassis 8. A tension is applied to the wire 16 by the tension application unit 30, the details of which will be discussed hereinafter.

The wire 16 in the present embodiment is in slidable contact with the top portions 14a of the element members 14 of the zigzag structure 13. In this case, a film made of a material having a small coefficient of friction against the wire 16, such as fluororesin, is desirably attached to or coated on the surfaces of the top portions 14a so as to reduce a friction force between the wire 16 and the top portions 14a of the element members 14. The same applies to the inner peripheral surface of the wire insertion member 18 firmly attached to the second member 12.

A guide tube preferably having the inner peripheral surface thereof formed of a material with a small coefficient of friction between the guide tube and the wire 16 may be firmly attached to the top portions 14a of the element members 14, and the wire 16 may be slidably inserted into the guide tube.

Referring now to FIG. 2 and FIG. 5, the cover member 20 is a member that covers both side surfaces of the zigzag structure 13 (both side surfaces in the direction orthogonal to the amplitude direction of the zigzag structure 13 and the direction of the amplitude centerline C). In the following description, the direction orthogonal to the amplitude direction of the zigzag structure 13 and the direction of the amplitude centerline C will be referred to as the thickness direction of the zigzag structure 13 in some cases.

According to the present embodiment, in order to make it possible to cover both side surfaces of the zigzag structure 13 independently of a bending state or the like of the zigzag structure 13, the cover member 20 is constituted by combining a plurality of cover elements so as to be capable of bending as the zigzag structure 13 bends.

Specifically, the cover member 20 is formed of a first cover element 21 that covers both side surfaces of the first member 11, a second cover element 22 that covers both side surfaces of the second member 12, and a third cover element 23 that covers both side surfaces of the zigzag structure 13 between the first cover element 21 and the second cover element 22.

The first cover element 21 also functions to cover both side surfaces of a portion of the zigzag structure 13 that is close to the first member 11. Similarly, the second cover element 22 also functions to cover both side surfaces of a portion of the zigzag structure 13 that is close to the second member 12.

The first cover element 21 has plate-like cover surfaces 21a, 21a opposing in parallel to each other with an interval provided therebetween in the thickness direction of the zigzag structure 13. Similarly, the second cover element 22 has plate-like cover surfaces 22a, 22a opposing in parallel to each other with an interval provided therebetween in the thickness direction of the zigzag structure 13. Similarly, the third cover element 23 has plate-like cover surfaces 23a, 23a opposing in parallel to each other with an interval provided therebetween in the thickness direction of the zigzag structure 13.

The interval between the cover surfaces 21a, 21a, the interval between the cover surfaces 22a, 22a, and the interval between the cover surfaces 23a, 23a are set to be slightly larger than the width in the thickness direction (thickness) of the zigzag structure 13.

Further, the first cover element 21, the second cover element 22, and the third cover element 23 are shaped like housings arranged substantially in the same direction as the direction of the amplitude centerline C of the zigzag structure 13.

Further, the end portion of the first cover element 21 that is adjacent to the third cover element 23 and the end portion of the second cover element 22 that is adjacent to the third cover element 23 are inserted into the third cover element 23.

Each of the cover surfaces 21a at the end portion of the first cover element 21 that is adjacent to the third cover element 23 is rotatably journaled by the cover surface 23a of the third cover element 23 that faces the cover surface 21a through a support shaft 24 having an axis in the thickness direction of the zigzag structure 13. Thus, the first cover element 21 is swingable about the axis of the support shaft 24 with respect to the third cover element 23.

Similarly, each of the cover surfaces 22a at the end portion of the second cover element 22 adjacent to the third cover element 23 is rotatably journaled by the cover surface 23a of the third cover element 23 that faces the cover surface 22a through a support shaft 25 having an axis in the thickness direction of the zigzag structure 13. Thus, the second cover element 22 is swingable about the axis of the support shaft 25 with respect to the third cover element 23.

The cover member 20 constituted of the first cover element 21, the second cover element 22, and the third cover element 23 as described above is externally inserted in the assembly of the first member 11, the second member 12 and the zigzag structure 13 such that the first member 11, the second member 12, and the zigzag structure 13 are positioned on the inner sides of the first cover element 21, the second cover element 22, and the third cover element 23, respectively, and the cover surfaces 21a, 21a, the cover surfaces 22a, 22a, and the cover surfaces 23a, 23a oppose both side surfaces of the first member 11, the second member 12, and the zigzag structure 13, respectively.

Further, each of the cover surfaces 21a of the first cover element 21 is provided with a slot 21c that linearly extends substantially in the same direction as the direction of the amplitude centerline C of the zigzag structure 13. A pin 11c protrusively provided from each side surface of the first member 11 (the surface opposing the slot 21c) is inserted in the slot 21c such that the pin 11c is slidable along the slot 21c. Thus, the first cover element 21 is supported by the first member 11 through the pin 11c so as to be movable relative to the first member 11 within the movable range of the pin 11c in the slot 21c.

Similarly, each of the cover surfaces 22a of the second cover element 22 is provided with a slot 22c that linearly extends substantially in the same direction as the direction of the amplitude centerline C of the zigzag structure 13. A pin 12c protrusively provided from each side surface of the second member 12 (the surface opposing the slot 22c) is inserted in the slot 22c such that the pin 12c is slidable along the slot 22c. Thus, the second cover element 22 is supported by the second member 12 through the pin 12c so as to be movable relative to the second member 12 within the movable range of the pin 12c in the slot 22c.

The joint mechanism main body 5 incorporates the cover member 20 as described above, so that the first cover element 21 and the second cover element 22 swing about the axes of the support shafts 24 and 25 corresponding thereto with respect to the third cover element 23 as the zigzag structure 13 bends (more specifically, as the zigzag structure 13 bends such that the top portions 14a of the element members 14 are placed on the outer side and the distal portions of the leg portions 14b are placed on the inner side).

This causes the cover member 20 to bend on the same side as the zigzag structure 13. As a result, the both side surfaces of the zigzag structure 13 are entirely covered by the cover member 20 independently of the bending state of the zigzag structure 13.

In this case, the deformation of the zigzag structure 13 is restricted to within the interval on the inner side of the cover member 20 in the thickness direction of the zigzag structure 13.

If the bending degree of the zigzag structure 13 increases, then the elastic force primarily attributable to the compression of the inter-leg-portion elastic members 15 increases, making it easy for the zigzag structure 13 to deform to bend in the direction about the axis in the amplitude direction thereof. Hereinafter, the bending deformation of the zigzag structure 13 will be referred to as the abnormal bending deformation.

However, the deformation of the zigzag structure 13 is restricted to within the interval on the inner side of the cover member 20 in the thickness direction of the zigzag structure 13 as described above, thus preventing the occurrence of the foregoing abnormal bending deformation of the zigzag structure 13. By extension, the bending of the zigzag structure 13 is restricted to bending in the direction about the axis in the thickness direction of the zigzag structure 13.

A description will now be given of the operation (function) of the joint mechanism main body 5 configured as described above.

In a state in which the wire 16 is being subjected to no tension or a sufficiently low tension, the elastic deformation of the element members 14 (especially the swings of the leg portions 14b relative to the top portions 14a) makes it possible to easily change both the pitch of the top portions on one side in the amplitude direction of the zigzag structure 13 and the pitch of the top portions on the other side.

In this state, the degree of freedom of deformation of the zigzag structure 13 is high. This state enables the zigzag structure 13 to deform according to the relative displacement of the first member 11 and the second member 12 without generating much elastic force between the first member 11 and the second member 12.

For example, if the second member 12 is rotationally displaced with respect to the first member 11 from the state illustrated in FIG. 2 to the state illustrated in FIG. 3, then the pitches of the top portions (the top portions 14a of the element members 14) on the wire 16 side of both sides in the amplitude direction of the zigzag structure 13 increase as illustrated in FIG. 3, thus minimizing the elastic deformation of the element members 14 and consequently minimizing the elastic deformation, i.e. the compression, of the inter-leg-portion elastic members 15, 15 between the pair of leg portions 14b, 14b of the element member 14.

In this case, the elastic force generated between the first member 11 and the second member 12 by the zigzag structure 13 will be sufficiently small.

Meanwhile, if the tension applied to the wire 16 is increased until the tension reaches a predetermined value or more, then the zigzag structure 13 is pressed along the wire 16 between the first member 11 and the second member 12, causing the adjacent leg portions 14b, 14b of the adjacent element members 14m, 14n of the zigzag structure 13 to overlap and come in contact with each other.

In this state, the pitches of the top portions (the top portions 14a of the element members 14) on the wire 16 side of both sides in the amplitude direction of the zigzag structure 13 are restrained from increasing, i.e. restrained to remain substantially constant, so that the degree of freedom of deformation of the zigzag structure 13 decreases.

In this state, if the zigzag structure 13 starts to be bent (more specifically, if the zigzag structure 13 starts to be bent such that the top portions 14a of the element members 14 of the zigzag structure are placed on the outer side and the distal portions of the leg portions 14b of the element members 14 are placed on the inner side), then the zigzag structure 13 generates a relatively large elastic force between the first member 11 and the second member 12. Further, the elastic force increases as the bending degree of the zigzag structure 13 increases.

For example, if the second member 12 is rotationally displaced with respect to the first member 11 from the state illustrated in FIG. 2 to the state illustrated in FIG. 4 while applying a high tension to the wire 16, then the pitches of the top portions (the top portions 14a of the element members 14) on the wire 16 side of both sides in the amplitude direction of the zigzag structure 13 are restrained from increasing as illustrated in FIG. 4, so that the element members 14 elastically deform to narrow the pitches of the top portions on the other side formed by the distal portions of the leg portions 14b of the element members 14 (consequently to narrow the interval between the distal portions of the pair of the leg portions 14b, 14b of the element member 14).

At the same time, the inter-leg-portion elastic members 15, 15 between a pair of leg portions 14b, 14b of each of the element members 14 are pressed against each other and compressed.

The zigzag structure 13 therefore generates a relatively large elastic force in the direction for canceling the bending between the first member 11 and the second member 12. Further, the elastic force increases as the bending degree of the zigzag structure 13 increases.

Thus, changing the tension applied to the wire 16 makes it possible to change the elastic force generated by the zigzag structure 13 between the first member 11 and the second member 12 when the zigzag structure 13 is bent as described above. Especially when the tension applied to the wire 16 is set to zero or a very small level, the elastic force generated by the zigzag structure 13 can be controlled to be sufficiently small.

If the tension applied to the wire 16 is increased, then a sufficiently large elastic force can be generated by the zigzag structure 13 according to the bending of the zigzag structure 13.

Further, in the state in which the tension applied to the wire 16 is increased to a predetermined value or more, the zigzag structure 13 is pressed along the wire 16 between the first member 11 and the second member 12. Hence, the adjacent leg portions 14b, 14b of the adjacent element members 14m, 14n of the zigzag structure 13 overlap and come in contact with each other. This makes it difficult for the adjacent leg portions 14b, 14b to twist, thus leading to higher stiffness in the direction about the axis in the amplitude direction of the zigzag structure 13. As a result, the possibility of the abnormal bending deformation of the zigzag structure 13 is minimized.

Figure 6A:
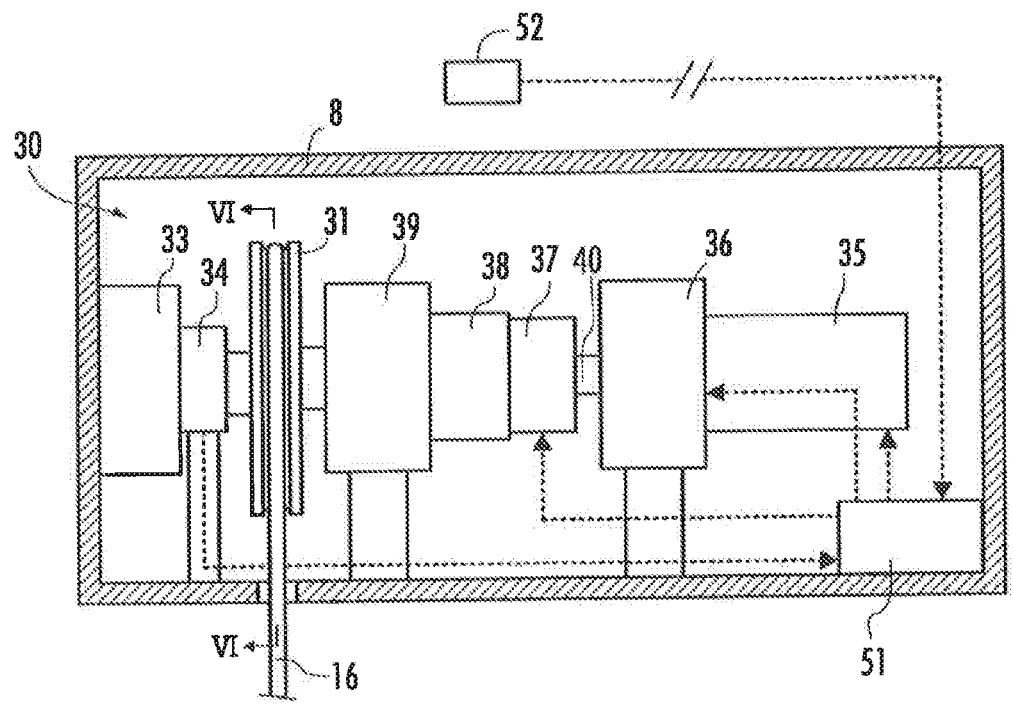
FIG. 6A is a diagram illustrating the configuration of a tension application unit of the joint mechanism of the first embodiment.
Figure 6B:
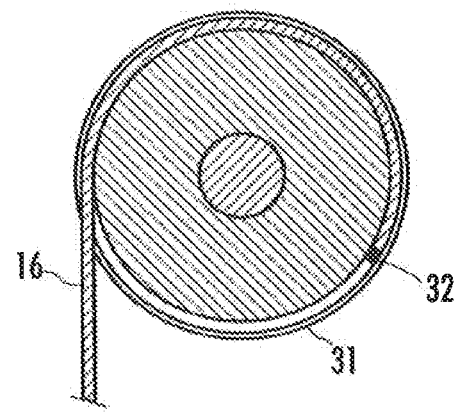
FIG. 6B is a sectional view taken along line VI-VI in FIG. 6A.

Referring now to FIG. 6A and FIG. 6B, a description will be given of the tension application unit 30, which applies a tension to the wire 16, and a configuration related to the control thereof.

The tension application unit 30 is provided for each of the legs 3 and housed in the chassis 8, as illustrated in FIG. 6A.

The tension application unit 30 is provided with a pulley 31 rotatably journaled through a bearing (not illustrated) in the chassis 8. The wire 16 is wound around the outer periphery of the pulley 31. In this case, the wire 16 is wound around the pulley 31 with an end thereof fixed to the outer periphery of the pulley 31 through a fastener 32, as illustrated in FIG. 6B. Further, the wire 16 is pulled out toward the second member 12 from the outer periphery of the pulley 31. Thus, a tension is applied to the wire 16 by rotationally driving the pulley 31 in the direction in which the wire 16 is rewound (in the clockwise direction in FIG. 6B).

A pre-tension generating unit 33 incorporating a spring, such as a torsion spring (not illustrated), is connected to one end side in the axial direction of the pulley 31, so that a rotational driving force in the direction of rewinding the wire 16 is applied to the pulley 31 from the pre-tension generating unit 33. In this case, the rotational driving force applied to the pulley 31 from the pre-tension generating unit 33 is a rotational driving force that is weak but sufficient to provide a tension (pre-tension) applied to the wire 16 to eliminate a slack of the wire 16.

Further, an angle detector 34 that detects the rotational angle of the pulley 31 is provided between the pre-tension generating unit 33 and the pulley 31. The angle detector 34 is constituted of a rotary encoder or a potentiometer and outputs signals based on the rotational angles of the pulley 31.

The other end side in the axial direction of the pulley 31 is connected to an electric motor 35 serving as an actuator. Operating the electric motor 35 to generate an output torque makes it possible to apply the rotational driving force in the rewinding direction of the wire 16 to the pulley 31 from the electric motor 35.

In this case, a brake unit 36, a clutch unit 37, a one-way clutch mechanism 38, and a reduction gear 39 are provided between the electric motor 35 and the pulley 31. The output torque of the electric motor 35 is transmitted to the pulley 31 through the intermediary of the brake unit 36, the clutch unit 37, the one-way clutch mechanism 38, and the reduction gear 39.

The brake unit 36 is a device for braking (stopping) the rotation of the pulley 31 as necessary. Further, the brake unit 36 can be selectively controlled between an ON state for braking a rotating shaft 40 (e.g. an output shaft of the electric motor 35) between the electric motor 35 and the pulley 31 and an OFF state for clearing the brake. The brake unit 36 may use, for example, a friction type brake unit that applies a braking force by a frictional force to the rotating shaft 40 or a lock unit that locks the rotating shaft 40 by recession-projection fitting or the like.

The clutch unit 37 is a device for cutting off the transmission of power between the electric motor 35 and the pulley 31, as necessary, and can be selectively controlled between the ON state for carrying out power transmission and the OFF state for cutting off the power transmission.

The one-way clutch mechanism 38 is a mechanism that blocks the transmission of power between the electric motor 35 and the brake unit 36 and the pulley 31 in the case where the rotational driving force in the direction of rewinding the wire 16 onto the pulley 31 is applied to the one-way clutch mechanism 38 from the output end thereof, i.e. the pulley 31 side (in the case where the input end of the one-way clutch mechanism 38 becomes a rotational load).

The reduction gear 39 is adapted to carry out speed change between the input end and the output end thereof and constituted of a gear mechanism having a plurality of gears or a wave gear device or the like.

The layout of the constituent elements of the tension application unit 30, including the pre-tension generating unit 33, the electric motor 35, the brake unit 36, the clutch unit 37, the one-way clutch mechanism 38, and the reduction gear 39 described above is not limited to the layout illustrated in FIG. 6A.

For example, the reduction gear 39 may be provided between the electric motor 35 and the brake unit 36. Further, the clutch unit 37, for example, may be provided more closely to the pulley 31 than the reduction gear 39, the electric motor 35, and the brake unit 36.

Further, the tension application unit 30 may be provided with a relay, which changes the extending direction of the wire 16 or has the same function as the pre-tension generating unit 33, in the middle of the running route of the wire 16 between the pulley 31 and the joint mechanism main body 5.

Figure 7:
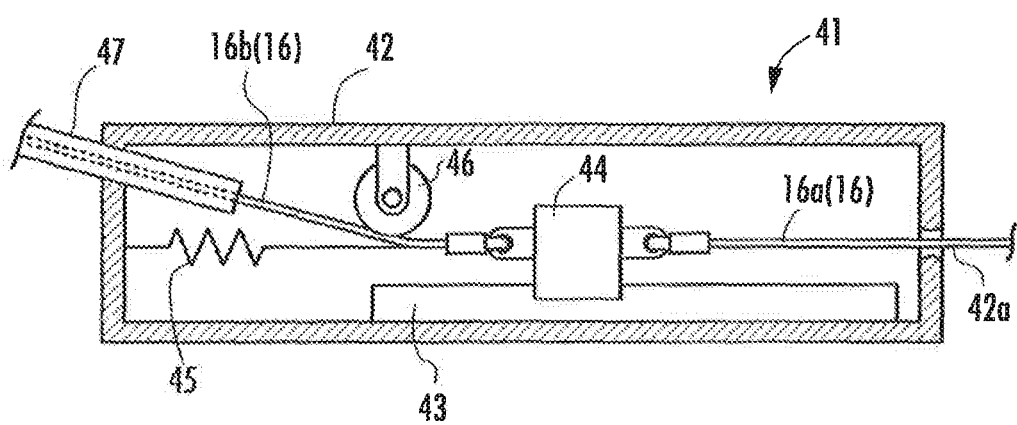
FIG. 7 is a diagram illustrating an example of a relay installed between the tension application unit and the main body of the joint mechanism.

FIG. 7 illustrates an example of the relay. A relay 41 includes, in a chassis 42, a guide rail 43, a movable section 44 that is slidable along the guide rail 43, and a spring 45 that generates a pre-tension elastic force.

The wire 16 is divided into a wire 16a on the joint mechanism main body 5 side and a wire 16b on the pulley 31 side. The ends of the wires 16a and 16b are pivotally attached to the movable section 44 in the chassis 42. In this case, the ends of the wires 16a and 16b, respectively, are extended from the movable section 44 in the same direction as that of the guide rail 43, i.e. the sliding direction of the movable section 44, but in the directions that are opposite from each other.

Further, in the relay 41 illustrated, the wire 16a, which is extended from the movable section 44 and which is on the joint mechanism main body 5 side, is led out of the chassis 42 through a hole 42a drilled in the chassis 42.

Further, the wire 16b on the pulley 31 side, which is extended from the movable section 44, has the extending direction thereof changed through the outer periphery of a guide roller 46 rotatably journaled in the chassis 42 and is led out of the chassis 42 through a tube 47.

The pre-tension spring 45 is connected to the movable section 44 so as to urge the movable section 44 in a direction for pulling the wire 16a on the joint mechanism main body 5 side (leftward in FIG. 7). The spring 45 applies a pre-tension, which is for eliminating a slack of the wire 16a, to the wire 16a on the joint mechanism main body 5 side.

The relay 41 illustrated in FIG. 7 is configured as described above.

The wire 16a on the joint mechanism main body 5 side may alternatively be led out of the chassis 42 through a tube as with the wire 16b on the pulley 31 side. Further, as with the wire 16b on the pulley 31 side, the wire 16a on the joint mechanism main body 5 side may have the extending direction thereof changed through a guide roller. Further alternatively, the wire 16b on the pulley 31 side may be led out of the chassis 42 merely through a hole drilled in the chassis 42.

Further, the type of the flexible lengthy member on the joint mechanism main body 5 side and the type of the flexible lengthy member on the pulley 31 side may be different. For example, one of the flexible lengthy members on the joint mechanism main body 5 side and the flexible lengthy member on the pulley 31 side may be composed of a wire and the other may be composed of a belt.

Referring back to FIG. 6A, the chassis 8, which houses the tension application unit 30, further houses a control unit 51 that controls the operations of the electric motor 35, the brake unit 36, and the clutch unit 37. Alternatively, however, the control unit 51 may be disposed at other location separate from the chassis 8, such as at the back surface of the waist-worn portion 2.

The control unit 51 is an electronic circuit unit that includes a CPU, a RAM, a ROM and the like. The control unit 51 receives the detection signals of the angle detector 34 and the detection signals of a ground contact sensor 52 that outputs signals indicating whether the foot-worn portion 1 on the same side as the leg 3 (left or right) having the joint mechanism main body 5 is in contact with the ground.

The ground contact sensor 52 is composed mainly of a pressure-sensitive switch or a pressure sensor attached to the bottom of the foot-worn portion 1, and outputs a signal, which indicates that the foot-worn portion 1 has come in contact with the ground, in response to a pressure applied to the ground contact sensor 52 when the foot-worn portion 1 comes in contact with the ground. The ground contact sensor 52 also outputs a signal, which indicates that the foot-worn portion 1 is no longer in contact with the ground (non-contact with the ground), when the foot-worn portion 1 leaves a floor and a pressure is no longer applied.

The foregoing pressure sensor is attached to the foot-worn portion 1 so as to detect the pressure between the bottom of the foot-worn portion 1 and the ground or the pressure applied to the sole of a person.

The control unit 51 is configured to control the operations of the electric motor 35, the brake unit 36, and the clutch unit 37 according to the outputs of the angle detector 34 and the ground contact sensor 52 by the functions implemented by executing an installed program or by the functions implemented by a hardware configuration.

A description will now be given of the operation of the joint mechanism 4 of the present embodiment, including the control processing by the control unit 51. The same operation of the joint mechanism 4 applies to both the left leg 3L and the right leg 3R. In the following description, therefore, the joint mechanism main body 5, the tension application unit 30, the control unit 51, a leg of a person and the like will correspond to either one of the legs 3, unless otherwise specified.

If the detection signal input from the ground contact sensor 52 is a signal indicating that the foot-worn portion 1 is not in contact with the ground, i.e. if the leg of the person to which the foot-worn portion 1 is attached is a swing leg, then the control unit 51 controls the clutch unit 37 to the OFF state (cutoff state) and also sets the electric motor 35 to a shutdown state (a state in which the supply of current to the electric motor 35 is interrupted).

At this time, the transmission of power between the pulley 31 and the electric motor 35 and the brake unit 36 is cut off, so that no rotational driving force is applied to the pulley 31 from the electric motor 35.

Thus, only a weak tension (pre-tension) applied by the pre-tension generating unit 33 or the spring 45 of the relay 41 is applied to the wire 16. This imparts a high degree of freedom of deformation to the zigzag structure 13 of the joint mechanism main body 5.

Hence, the zigzag structure 13 smoothly deforms to bend according to the relative displacements of the first member 11 and the second member 12 caused by the bending of the leg of the person that has become the swing leg. The zigzag structure 13 bends as illustrated in, for example, FIG. 3.

At this time, the bending of the zigzag structure 13 is not the bending on a fixed single joint axis, thus preventing the person from feeling uncomfortable or restrained when the person bends the leg at the knee joint.

Further, in this case, the elastic force generated at the zigzag structure 13 remains zero or sufficiently small. In addition, the rotation of the pulley 31 is not transmitted to the electric motor 35 and therefore the rotor of the electric motor 35 will not rotate in conjunction with the pulley 31, making it possible to suppress the rotational resistance of the pulley 31 to a small value. This prevents the person from feeling an excess resistance when the person bends or stretches the swing leg.

Alternatively, the clutch unit 37 may be turned on in the state in which the leg of the person to which the foot-worn portion 1 is attached is the swing leg, and the electric motor 35 may be operated such that the electric motor 35 outputs a rotational driving force that causes a tension approximately as weak as a pre-tension (a tension of a predetermined value or less) to be applied to the wire 16 in the state in which the brake unit 36 is off.

In such a case, the clutch unit 37 may be omitted.

Further, if the detection signal received from the ground contact sensor 52 is the signal indicating that the foot-worn portion 1 is in contact with the ground, i.e. if the leg of the person to which the foot-worn portion 1 is attached is a supporting leg, then the control unit 51 controls the operation of the electric motor 35 so as to apply a tension of a predetermined value or more, which is larger than the pre-tension, to the wire 16 from the electric motor 35 while controlling the clutch unit 37 to an ON state and also controlling the brake unit 36 to the OFF state.

Specifically, the control unit 51 controls the current supplied to the electric motor 35 so as to generate an output torque of a predetermined magnitude in the electric motor 35.

In this case, the output torque to be generated in the electric motor 35 is a torque having a magnitude of a predetermined value or more that enables a tension applied to the wire 16 to cause the adjacent leg portions 14b, 14b of the adjacent element members 14m, 14n of the zigzag structure 13 to overlap and come in contact with each other (to restrict the pitches of the top portions on the wire 16 side of the both sides in the amplitude direction of the zigzag structure 13 to be substantially constant).

Thus, by controlling the operation of the electric motor 35, a tension of a predetermined value or more, which makes it possible to cause the adjacent leg portions 14b, 14b of the adjacent element members 14m, 14n of the zigzag structure 13 to overlap and come in contact with each other, is applied to the wire 16.

In this state, if the zigzag structure 13 starts to be bent as illustrated in FIG. 4, then the zigzag structure 13 generates a relatively large elastic force (an elastic force acting to cancel the bending of the zigzag structure 13) between the first member 11 and the second member 12 as described above. The elastic force increases as the bending degree of the zigzag structure 13 increases.

Accordingly, if the person bends a supporting leg (if the person lowers his or her waist), then a force in the direction for stretching the supporting leg acts on the supporting leg. This enables a person with weak legs to easily support his or her upper body when sitting on a chair, squatting or standing up from a chair or from a squatting posture.

In this case also, as with the case where no rotational driving force is applied to the pulley 31 from the electric motor 35, the bending of the zigzag structure 13 is not the bending on a fixed single joint axis, thus preventing the person from feeling uncomfortable or restrained when the person bends the leg at the knee joint.

Further, in the present embodiment, the inter-leg-portion elastic members 15, 15 between the pair of leg portions 14b, 14b of each of the element members 14 of the zigzag structure 13 are separated on one side and the other side of the leg portions 14b, 14b, so that the inter-leg-portion elastic members 15, 15 come in contact by being pressed against each other.

In this case, the possibility of slippage attributable to the lateral strain between the inter-leg-portion elastic members 15, 15 is minimized, thus restraining each other. This prevents an excess force attributable to a friction force from being generated between the first member 11 and the second member 12 when the zigzag structure 13 bends. As a result, the bending deformation of the zigzag structure 13 is smoothly accomplished.

In the case where the operation of the electric motor 35 is controlled as described above in the state wherein a leg of the person has become the supporting leg, the brake unit 36 may be omitted. Alternatively, the brake unit 36 may be actuated, as appropriate, in place of applying the rotational driving force to the pulley 31 from the electric motor 35.

For example, in the state wherein a leg of the person has become the supporting leg, the rotational driving force is applied to the pulley 31 from the electric motor 35 to increase the tension applied to the wire 16 by the electric motor 35 and then the brake unit 36 is controlled to the ON state to brake the rotation of the pulley 31. This allows the tension applied to the wire 16 to remain high.

In this case, it is unnecessary to generate the output torque of the electric motor 35 while the brake unit 36 is in the ON state, so that the supply of current to the electric motor 35 can be stopped. Hence, the power consumption or heat generation of the electric motor 35 can be suppressed.

Supplementarily, the present embodiment is provided with the one-way clutch mechanism 38. Therefore, even in the state wherein the braking force for blocking the rotation of the pulley 31 (specifically, the rotation in the direction of pulling out the wire 16 from the pulley 31) is being applied from the electric motor 35 or the brake unit 36, if a slack occurs in the wire 16, then the rotational driving force of the pre-tension generating unit 33 causes the pulley 31 to rotate, thereby eliminating the slack of the wire 16.

Second Embodiment

Figure 8A:
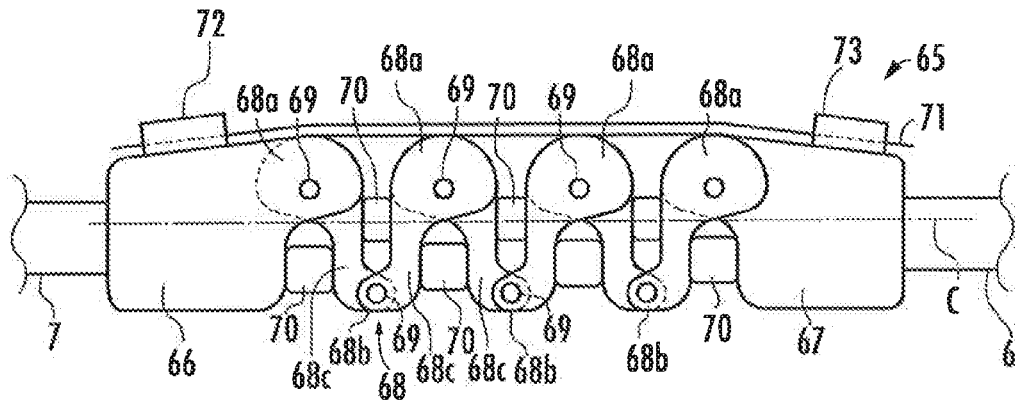
FIG. 8A, FIG. 8B and FIG. 8C are diagrams illustrating the configuration of an essential section of a main body of a joint mechanism of a second embodiment.
Figure 8B:
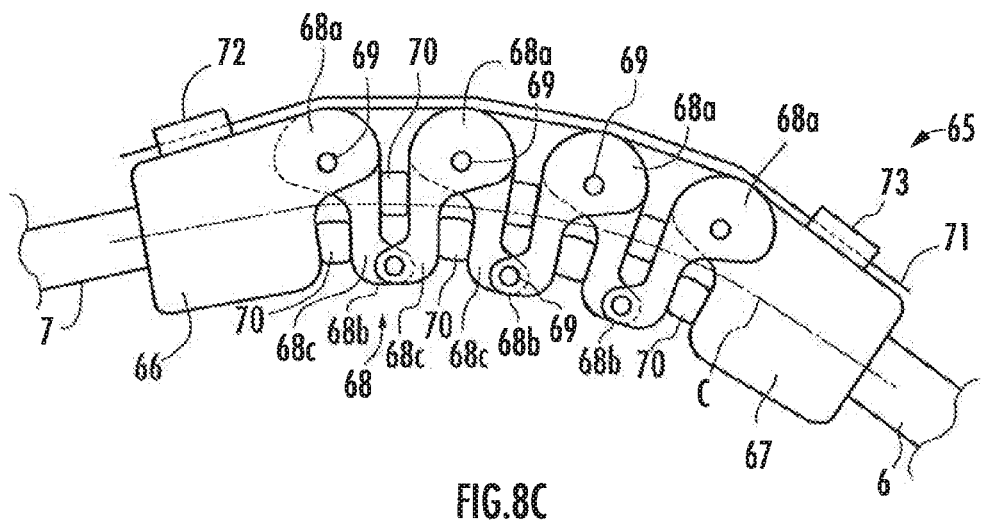
Figure 8C:
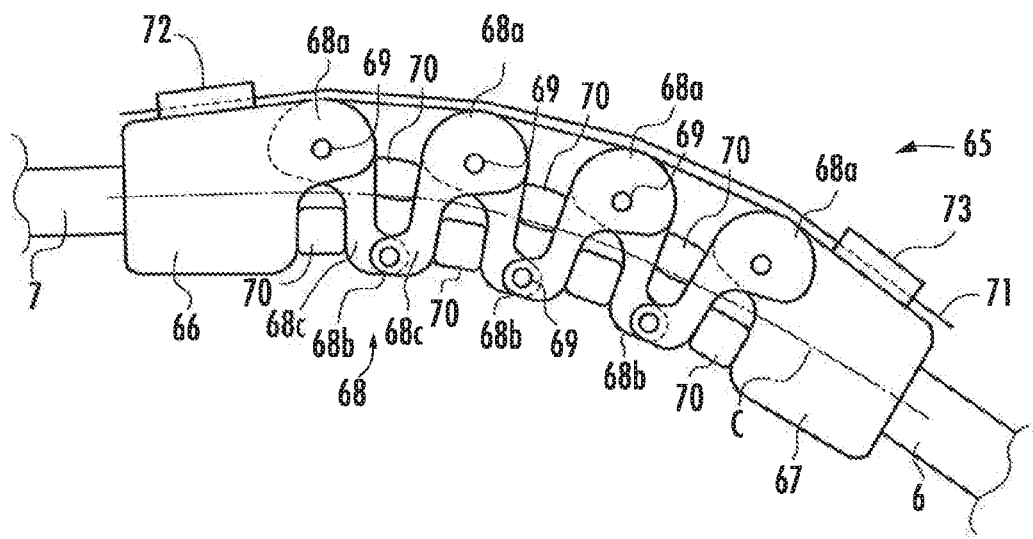

Referring now to FIG. 8A, FIG. 8B and FIG. 8C, a second embodiment of the present invention will be described. The joint mechanism of the present embodiment differs from the foregoing embodiment only in the configuration of a joint mechanism main body. For this reason, the description of the present embodiment will be focused on the aspects that are different from the first embodiment, and the description of the same aspects as those of the first embodiment will be omitted.

As illustrated in FIG. 8A, FIG. 8B and FIG. 8C, a joint mechanism main body 65 of the present embodiment includes a first member 66 having the lower frame 7 extended therefrom, a second member 67 having the upper frame 6 extended therefrom, and a zigzag structure 68 that extends in a zigzag pattern from the first member 66 toward the second member 67 and which connects the first member 66 and the second member 67 in a relatively displaceable manner.

The first member 66 and the second member 67 are highly rigid members made of a metal or a resin, as with the first embodiment.

In the zigzag structure 68 of the present embodiment, a pair of leg portions 68c, 68c extending in a bifurcated manner from a top portion 68a on one side in the amplitude direction of the zigzag structure 68 and from a top portion 68b on the other side are connected through a support shaft 69, which is provided in the top portion 68a or 68b between the leg portions 68c, 68c, such that the leg portions 68c, 68c are relatively swingable about the axis of the support shaft 69.

The leg portions 68c in the present embodiment are made of a metal or a resin and highly rigid. The axes of the support shafts 69 are in a direction orthogonal to the amplitude direction of the zigzag structure 68 and the direction of an amplitude centerline C (in the direction perpendicular to the paper surface in FIG. 8A, FIG. 8B and FIG. 8C).

The leg portion 68c that connects any one of the top portions 68a on one side in the amplitude direction of the zigzag structure 68 and one of the top portions 68b on the other side is the leg portion 68c that is shared by both the top portions 68a and 68b.

In other words, therefore, the zigzag structure 68 has a structure in which a plurality of the leg portions 68c are connected in order in the zigzag pattern with the support shafts 69 provided on both end sides thereof, and the leg portions 68c, 68c interconnected at each connecting portion, i.e. the top portion 68a or 68b, are relatively swingable about the axis of the support shaft 69 at the connecting portion.

In the present embodiment, the leg portion 68c closest to the first member 66 is connected swingably with respect to the first member 66 through the support shaft 69. In this case, the connecting portion of the first member 66 and the leg portion 68c is also regarded as a top portion, and the first member 66 is regarded to constitute a leg portion connected with the leg portion 68c through the top portion.

Similarly, the connecting portion of the leg portion 68c closest to the second member 67 and the second member 67 is also regarded as a top portion, and the second member 67 is regarded to constitute a leg portion connected with the leg portion 68c through the top portion.

Supplementarily, the zigzag structure 68 in the present embodiment has a plurality of top portions 68a, 68b on one side and the other side, respectively, in the amplitude direction. Alternatively, however, there may be a single top portion 68a on one side or a single top portion 68b on the other side. In this case, the connecting portion of one of the two leg portions 68c, 68c, which extend in the bifurcated manner through the support shaft 69 from the single top portion 68a or 68b, and the first member 66, and the connecting portion of the other of the two leg portions 68c, 68c and the second member 67 can be regarded as the two top portions on the opposite side from the single top portion 68a or 68b.

Further, in the present embodiment, inter-leg-portion elastic members 70, 70 firmly attached to the opposing surfaces of the pair of leg portions 68c, 68c (corresponding to the first elastic member and the second elastic member in the present invention) are provided, facing against each other, between the pair of leg portions 68c, 68c extending in the bifurcated manner from the top portions 68a and 68b of the zigzag structure 68. The inter-leg-portion elastic members 70 are elastic members made of rubber and shaped like, for example, a rectangular parallelepiped.

Further, the thickness of each of the inter-leg-portion elastic members 70, 70 between the pair of the leg portions 68c, 68c extending from the top portions 68a and 68b is set such that the inter-leg-portion elastic members 70, 70 are pressed against each other to generate an elastic force in the direction for increasing the interval between the pair of the leg portions 68c, 68c when the pair of the leg portion 68c, 68c are relatively swung to decrease the interval between the pair of the leg portions 68c, 68c.

In the zigzag structure 68 configured as described above, the leg portions 68c, 68c connected at the top portions 68a and 68b through the support shafts 69 are relatively swung, thus making it possible to change one or both of the pitch of the top portions on one side in the amplitude direction of the zigzag structure 68 and the pitch of the top portions on the other side.

This arrangement enables the zigzag structure 68 to expand or contract to change the length of the zigzag structure 68 in the direction of the amplitude centerline C or enables the zigzag structure 68 to bend to change the bending degree of the amplitude centerline C.

FIG. 8A illustrates the zigzag structure 68 in a state in which the zigzag structure 68 has contracted in the direction of the amplitude centerline C while both the inter-leg-portion elastic members 70, 70 between the leg portions 68c, 68c, which are connected at the top portions 68a and 68b through the support shafts 69, are being compressed, and in which the amplitude centerline C is substantially straight.

Further, FIG. 8B illustrates the zigzag structure 68 in a state in which the zigzag structure 68 has contracted in the direction of the amplitude centerline C while both the inter-leg-portion elastic members 70, 70 between the leg portions 68c, 68c, which are connected at the top portions 68a and 68b through the support shafts 69, are being compressed, and in which the amplitude centerline C is bent.

Further, FIG. 8C illustrates the zigzag structure 68 in a state in which the zigzag structure 68 has stretched in the direction of the amplitude centerline C such that the inter-leg-portion elastic members 70, 70 between the leg portions 68c, 68c, which are connected at the top portions 68a and 68b through the support shafts 69, are not compressed much and in which the amplitude centerline C is bent.

Further, a flexible lengthy member 71 is extended from the first member 66. The flexible lengthy member 71 is, for example, a wire, as with the first embodiment. Hereinafter, the flexible lengthy member 71 will be referred to as the wire 71. However, the flexible lengthy member 71 may alternatively be, for example, a belt.

The wire 71 is disposed to extend in substantially the same direction as the direction of the amplitude centerline C from the first member 66 toward the second member 67 (extends along the row of the top portions 68a) on the outer side of, for example, the top portions 68a on one side among the top portions 68a or 68b on both sides in the amplitude direction of the zigzag structure 68.

Further, as with the first embodiment, the end of the wire 71 on the first member 66 side is fixed to the first member 66 through a wire fixing member 72 in which the end is inserted. The portion of the wire 71 that opposes the second member 67 is slidably inserted in a wire insertion member 73 firmly attached to the second member 67, as with the first embodiment. Accordingly, the wire 71 is travelable with respect to the second member 67.

Further, as with the first embodiment, the wire 71 is connected to the tension application unit 30 and subjected to a tension applied by the tension application unit 30.

In the present embodiment, the wire 71 comes in slidable contact with the top portions 68a on one side in the amplitude direction of the zigzag structure 68. In this case, as with the case described in connection with the first embodiment, a film made of a material having a small coefficient of friction against the wire 71, such as fluororesin, is desirably attached to or coated on the surfaces of the top portions 68a so as to reduce a friction force between the wire 71 and the top portions 68a.

A guide tube having the inner peripheral surface thereof preferably formed of a material with a small coefficient of friction between the guide tube and the wire 71 may be firmly attached to the top portions 68a on one side in the amplitude direction of the zigzag structure 68, and the wire 71 may be slidably inserted into the guide tube.

The configuration of the joint mechanism of the present embodiment is the same as that of the first embodiment except for the aspects described above. In the present embodiment, however, the cover member that covers the zigzag structure 68 is unnecessary. However, the joint mechanism main body 65 may be provided with a cover member similar to that in the first embodiment in order to mainly prevent foreign substances from entering the zigzag structure 68.

The joint mechanism main body 65 configured as described above provides the same functions as those of the joint mechanism main body 5 in the first embodiment by changing the tension applied to the wire 71.

In a state in which the wire 71 is being subjected to no tension or a sufficiently low tension, the zigzag structure 68 has a high degree of freedom of deformation. In this state, the swings of the leg portions 68c at the top portions 68a and 68b of the zigzag structure 68 make it possible to easily change both the pitch of the top portions 68a on one side in the amplitude direction of the zigzag structure 68 and the pitch of the top portions 68b on the other side. This enables the zigzag structure 68 to deform according to the relative displacement of the first member 66 and the second member 67 while hardly generating an elastic force between the first member 66 and the second member 67.

For example, the rotational displacement of the second member 67 with respect to the first member 66 from the state illustrated in FIG. 8A to the state illustrated in FIG. 8C allows the pitch of the top portions 68a on one side in the amplitude direction of the zigzag structure 68 and the pitch of the top portions 68b on the other side to increase, as illustrated in FIG. 8C. Hence, there will be no or a very small elastic deformation, i.e. the compression, of the inter-leg-portion elastic members 70, 70 between each pair of leg portions 68c, 68c.

In this case, the elastic force generated between the first member 66 and the second member 67 by the zigzag structure 68 will be zero or sufficiently small.

Meanwhile, if the tension applied to the wire 71 is increased until the tension reaches a predetermined value or more, then the zigzag structure 68 is pressed along the wire 71 between the first member 66 and the second member 67. Hence, the inter-leg-portion elastic members 70, 70 between the leg portions 68c, 68c extending especially from the top portions 68b on the opposite side from the wire 71 are compressed.

In this state, the pitch of the top portions 68a on the wire 71 side of both sides in the amplitude direction of the zigzag structure 68 is restrained from increasing, i.e. restrained to remain substantially constant, so that the degree of freedom of deformation of the zigzag structure 68 decreases.

In this state, if the zigzag structure 68 starts to be bent (more specifically, if the zigzag structure 68 starts to be bent such that the top portions 68a of the zigzag structure 68 on the wire 71 side are placed on the outer side and the top portions 68b on the opposite side are placed on the inner side), then a relatively large elastic force is generated between the first member 66 and the second member 67. The elastic force increases as the bending degree of the zigzag structure 68 increases.

For example, if the second member 67 is rotationally displaced with respect to the first member 66 from the state illustrated in FIG. 8A to the state illustrated in FIG. 8B while applying a high tension to the wire 71, then the zigzag structure 68 bends such that the interval between the leg portions 68c, 68c extending from the top portions 68a on the wire 71 side decreases, as illustrated in FIG. 8B. Consequently, the inter-leg-portion elastic members 70, 70 between the leg portions 68c, 68c are compressed.

As a result, the zigzag structure 68 generates a relatively large elastic force between the first member 66 and the second member 67. The elastic force increases as the bending degree of the zigzag structure 68 increases.

Accordingly, as with the first embodiment, changing the tension applied to the wire 71 makes it possible to change the elastic force generated by the zigzag structure 68 between the first member 66 and the second member 67 when the zigzag structure 68 is bent. Especially when the tension applied to the wire 71 is set to zero or a very small level, the zigzag structure 68 will not generate an elastic force or will generate a very small elastic force.

If the tension applied to the wire 71 is increased, then a sufficiently large elastic force can be generated by the zigzag structure 68 according to the bending of the zigzag structure 68.

Further, in the joint mechanism according to the present embodiment, the control of the operation of the tension application unit 30 is the same as that in the first embodiment.

In a state in which a leg of the person has become a swing leg, i.e. a foot-worn portion 1 is not in contact with the ground, no tension in the direction for rewinding the wire 71 onto the pulley 31 will be applied to the wire 71 by the electric motor 35 or the brake unit 36, and only a pre-tension is applied by a pre-tension generating unit 33 or a spring 45 of a relay 41.

Thus, as with the first embodiment, the zigzag structure 68 smoothly deforms to bend according to the relative displacement of the first member 66 and the second member 67 as the leg of the person, which has become the swing leg, bends or stretches.

Further, at this time, the bending of the zigzag structure 68 is not the bending on a fixed single joint axis, thus preventing the person from feeling uncomfortable or restrained when the person bends the leg at the knee joint.

Further, in a state in which a leg of the person has become a supporting leg, i.e. the foot-worn portion 1 is in contact with the ground, a large tension of a predetermined value or more in the direction of rewinding the wire 71 onto the pulley 31 is applied to the wire 71 by the electric motor 35 or the brake unit 36.

The tension applied to the wire 71 in this case is sufficiently high to fully compress the inter-leg-portion elastic members 70, 70 between the leg portions 68c, 68c extending from the top portions 68b on the opposite side from the wire 71.

In this state, if the zigzag structure 68 starts to be bent, then the zigzag structure 68 generates a relatively large elastic force (an elastic force acting to cancel the bending of the zigzag structure 68) between the first member 66 and the second member 67 as described above. The elastic force increases as the bending degree of the zigzag structure 68 increases.

Accordingly, as with the first embodiment, if the person bends the supporting leg (if the person lowers his or her waist), then a force in the direction for stretching the supporting leg acts on the supporting leg. This enables a person with weak legs to easily support his or her upper body when sitting on a chair, squatting or standing up from a chair or from a squatting posture.

In this case also, the bending of the zigzag structure 68 is not the bending on a fixed single joint axis, thus preventing the person from feeling uncomfortable or restrained when the person bends the leg at the knee joint.

[Modifications]

The following will describe several modifications of the embodiments described above.

In the foregoing first embodiment, the adjacent leg portions 14*b*, 14*b* of the adjacent element members 14, 14 (14*m*, 14*n*) of the zigzag structure 13 have been connected by welding or bonding. Alternatively, however, the adjacent leg portions 14*b*, 14*b* may be fastened using screws or the like.

Figure 9:
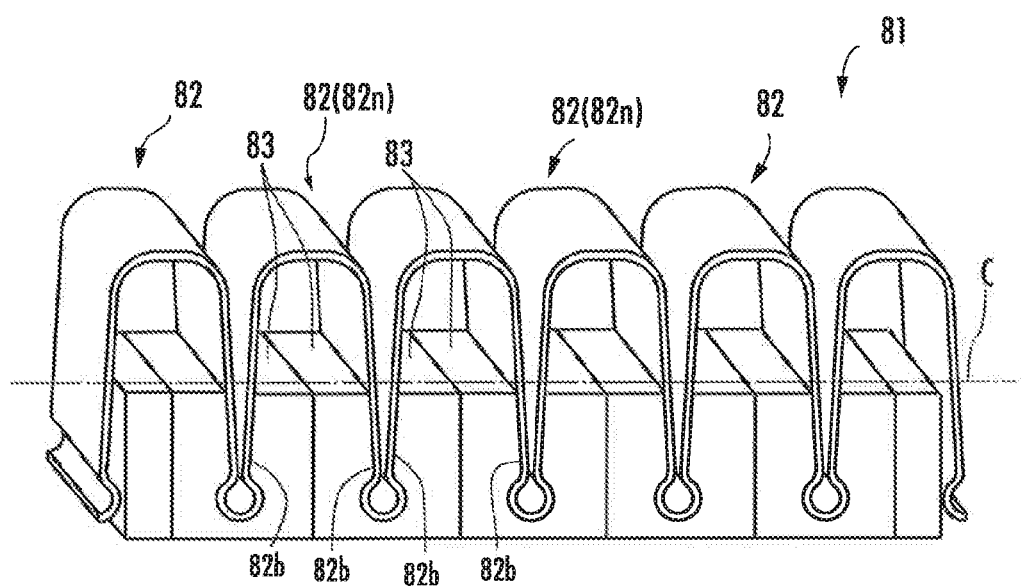
FIG. 9 to FIG. 12 are diagrams illustrating examples of zigzag structures of modifications.

Further, the zigzag structure may be composed of a plurality of element members continuously connected into one piece by machining or forming a single plate-like elastic member. For example, the zigzag structure may be configured like a zigzag structure 81 as illustrated in FIG. 9. In this example, in the row of a plurality of element members 82 (U-shaped or rectangular element members 82) constituting the zigzag structure 81, the distal ends of the adjacent leg portions 82*b*, 82*b* of the adjacent element members 82 (82*m*), 82 (82*n*) are continuously connected through the top portions rounded approximately into tubular shapes.

In the example illustrated in FIG. 9, as with the zigzag structure 13 in the first embodiment, elastic members (inter-leg-portion elastic members) 83, 83 are provided between a pair of the leg portions 82*b*, 82*b* of each of the element members 82. However, the inter-leg-portion elastic members 83, 83 may be omitted. Further, in the example illustrated in FIG. 9, the inter-leg-portion elastic members 83 firmly attached to the adjacent leg portions 82*b*, 82*b* of the adjacent element members 82 (82*m*), 82 (82*n*) are integrally connected. However, as with the first embodiment, the inter-leg-portion elastic members 83 firmly attached to the leg portions 82*b* and 82*b*, respectively, may be provided as separate members.

Figure 10:
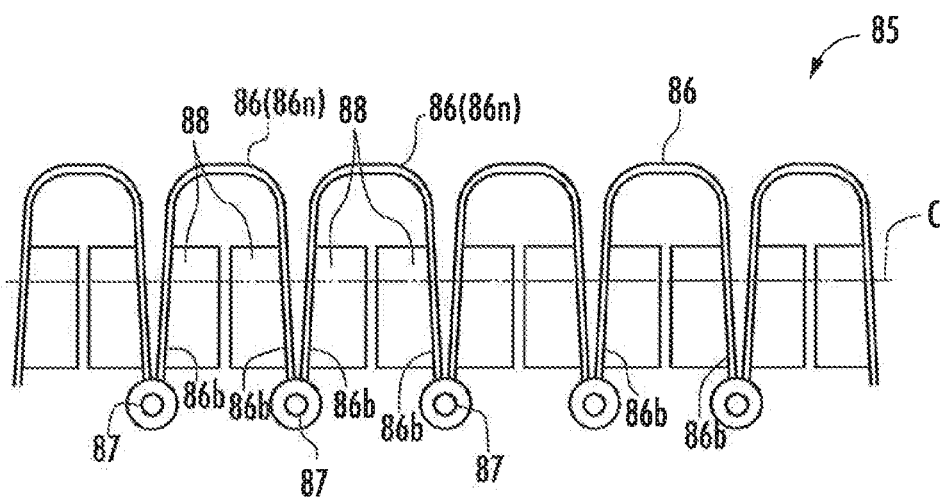

Further, as illustrated in FIG. 10, in the row of the plurality of element members 86 (the U-shaped or rectangular element members 86) constituting a zigzag structure 85, the distal ends of the adjacent leg portions 86*b*, 86*b* of the adjacent element members 86, 86 (86*m*, 86*n*) may be swingably interconnected through a support shaft 87 having an axis that is orthogonal to the amplitude direction of the zigzag structure 85 and the direction of the amplitude centerline.

In the example illustrated in FIG. 10, elastic members (inter-leg-portion elastic members) 88, 88 are provided between the pair of the leg portions 86*b*, 86*b* of each of the element members 86, as with the zigzag structure 13 in the first embodiment. However, the inter-leg-portion elastic members 88, 88 may be omitted.

Further, the zigzag structure may be configured such that the stiffness of the zigzag structure against bending changes in the direction of the amplitude centerline of the zigzag structure. For example, in the zigzag structure 13 of the first embodiment, the stiffness of the inter-leg-portion elastic members 15 may be set such that the inter-leg-portion elastic members 15 closer to the center between the first member 11 and the second member 12, i.e. the center in the direction of the amplitude centerline C, exhibit higher stiffness.

This arrangement allows the inter-leg-portion elastic members 15 to develop uniform strain when the zigzag structure 13 is deformed to bend (more specifically, when the zigzag structure 13 is deformed to bend such that the top portions 14*a* of the element members 14 are placed on the outer side and the distal ends of the leg portions 14*b* are placed on the inner side). It is possible, therefore, to prevent undue strain from occurring in any one of the inter-leg-portion elastic members 15 (especially the inter-leg-portion elastic members 15 in the vicinity of the center between the first member 11 and the second member 12), as compared with the remaining inter-leg-portion elastic members 15. This permits prolonged lives of the inter-leg-portion elastic members 15. Further, variations in the lives of the inter-leg-portion elastic members 15 can be prevented.

The arrangement in which the stiffness of the inter-leg-portion elastic members of the zigzag structure that are closer to the center in the direction of the amplitude centerline of the zigzag structure is set to be higher as described above can be applied, in the same manner, to the zigzag structure 68 having the structure in the second embodiment or the zigzag structure 81 or 85 having the structure illustrated in FIG. 9 or FIG. 10.

Further, even in the case where the inter-leg-portion elastic members have the same stiffness, the stiffness against the bending of the zigzag structure can be changed in the direction of the amplitude centerline of the zigzag structure by using, for example, the method described below.

Figure 11:
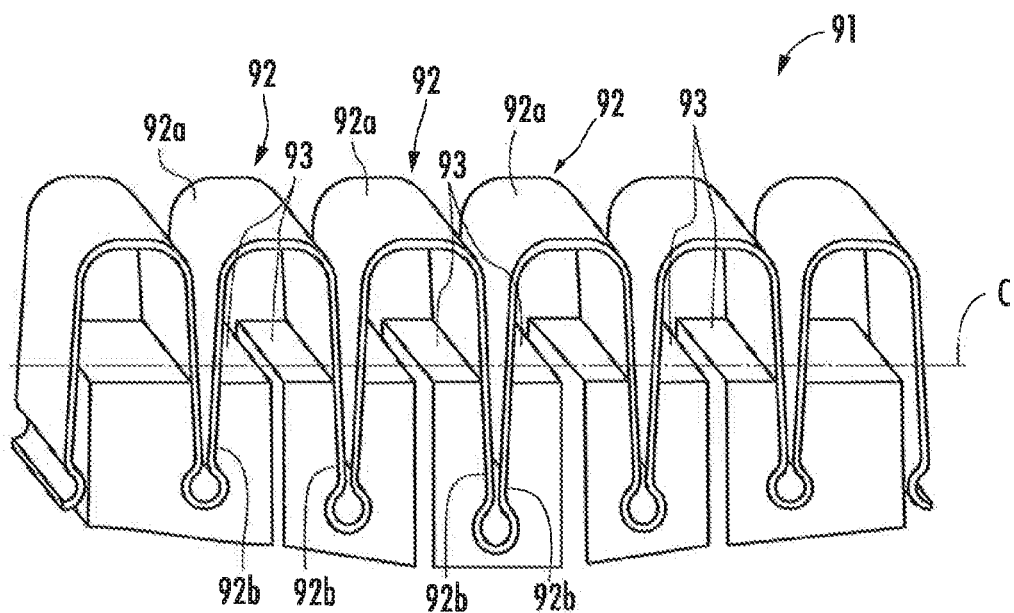

For example, in a zigzag structure 91 constituted of a plurality of U-shaped or rectangular element members 92 illustrated in FIG. 11, the leg portions 92*b* of the element members 92 that are closer to the center in the direction of an amplitude centerline C of the zigzag structure 91 are set to be longer. Further, regarding inter-leg-portion elastic members 93 provided between the leg portions 92*b*, 92*b* of each of the element members 92, the inter-leg-portion elastic members 93 that are closer to the foregoing center are set to be longer toward the distal ends of the leg portions 92*b*.

This arrangement of the inter-leg-portion elastic members 93 makes it possible to further increase a force or moment that acts to cancel the bending of the zigzag structure 91 by the elastic force of the inter-leg-portion elastic members 93 as the positions of the inter-leg-portion elastic members 93 are closer to the center in the direction of the amplitude centerline C of the zigzag structure 91 when the zigzag structure 91 is deformed to bend (more specifically, when the zigzag structure 91 is deformed to bend such that top portions 92*a* of the element members 92 are placed on the outer side and the distal ends of the leg portions 92*b* are placed on the inner side).

As a result, the substantial stiffness of the portions closer to the center in the direction of the amplitude centerline C increases against the bending deformation of the zigzag structure 91.

The zigzag structure 91 illustrated in FIG. 11 is the same type as that illustrated in FIG. 9. The arrangement of the inter-leg-portion elastic members 93 in the zigzag structure 91 illustrated in FIG. 11 can be applied in the same manner to the zigzag structure 13 or 68 having the structure of the first embodiment or the second embodiment or the zigzag structure 85 having the structure illustrated in FIG. 10.

Further, in the zigzag structure 13 of the first embodiment or a zigzag structure having a structure as the structure of the zigzag structure 81 illustrated in FIG. 9, the foregoing abnormal bending deformation tends to take place as the bending degree of the zigzag structure increases. In order to prevent the abnormal bending deformation, stopper members, for example, may be provided between a pair of leg portions of each element member so as to block further bending deformation of the zigzag structure by the stopper when the bending degree of the zigzag structure increases.

Figure 12:
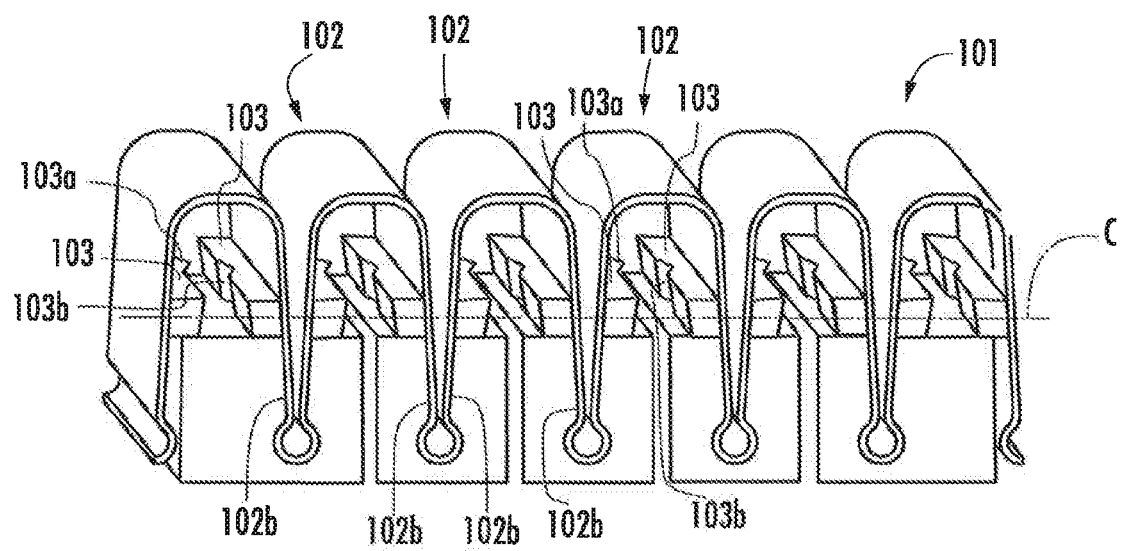

An example of the stopper members is illustrated in FIG. 12. In a zigzag structure 101, a pair of stopper members 103, 103 are firmly attached to the opposing surfaces of a pair of leg portions 102b, 102b and are provided between the leg portions 102b, 102b of each of U-shaped or rectangular element members 102 constituting the zigzag structure 101.

When the bending degree of the zigzag structure 101 increases to a certain extent, the stopper members 103, 103 between the leg portions 102b, 102b of each of the element members 102 come in contact with each other. This blocks the interval between the leg portions 102b, 102b from further decreasing, thereby preventing the zigzag structure 101 from further bending.

Further, in the zigzag structure 101 illustrated, when the stopper members 103, 103 between the pair of the leg portions 102b, 102b of each of the element members 102 come in contact, a projecting portion 103a protrusively provided on one of the stopper members 103, 103 and a recessed portion 103b formed in the other thereof fit with each other. This restricts the mutual relative displacement of the stopper members 103, 103.

This arrangement makes it possible to effectively prevent the zigzag structure 101 from developing the abnormal bending deformation.

The stopper members 103 described above may be applied to, for example, the zigzag structure 13 having the structure described in the first embodiment. Further, the stopper members 103 provided between the pair of leg portions 102b, 102b of each of the element members 102 may be firmly attached to only one of the pair of leg portions 102b, 102b. The same applies to the zigzag structure 13 having the structure described in the first embodiment.

Further, in the foregoing first embodiment, the cover member 20 for preventing the abnormal bending deformation of the zigzag structure 13 has been composed of a plurality of cover elements, namely, the first cover element 21, the second cover element 22, and the third cover element 23. Alternatively, however, the cover member may be composed of a single cover element. In this case, however, both side surfaces in the thickness direction of the zigzag structure 13 are covered independently of the bending degree of the zigzag structure 13, so that the area of the cover member will be larger. Hence, the cover member is preferably constituted of a plurality of cover elements, as with the foregoing first embodiment.

Further, in order to enhance the effect for preventing the occurrence of the abnormal bending deformation of the zigzag structure 13 by the cover member 20, the cover member 20 may be pressed against the side surfaces of a knee of a leg of a person, and the cover member 20 (specifically, for example, the foregoing third cover element 23) may be bound onto the knee of the leg of the person by an elastic fabric or mesh type member like a knee pad.

Further, the walking assist device A described in the foregoing first embodiment has only one leg 3 provided with the joint mechanism main body 5 for each leg of a person. Alternatively, however, the walking assist device may be configured to have legs 110, 110 extended along the outer side and the inner side of each leg of a person as illustrated in FIG. 13.

Figure 13:
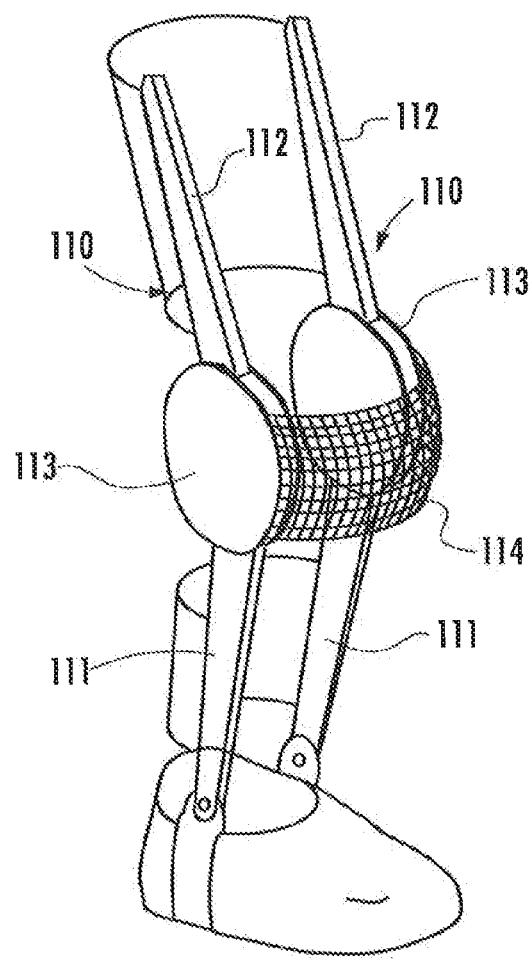
FIG. 13 is a perspective view illustrating another example of a walking assist device.

In the walking assist device illustrated in FIG. 13, the joint mechanism main body (not illustrated) between a lower frame 111 and an upper frame 112 of each of the legs 110 is covered by a single cover member 113. Further, a mesh type knee pad 114 for pressing the cover members 113 against the knee of the person is attached to the cover members 113.

The configuration of the joint mechanism main body may be provided with a zigzag structure having any one of the structures described above.

Further, in the walking assist device, a device that applies a tension to a wire, i.e. a flexible lengthy member (not illustrated), of the two legs 110, 110 corresponding to each leg of the person may be separately provided. Alternatively, the tension may be applied to the wire by distributing a rotational driving force through a gear from the same electric motor or brake unit to a pulley that rewinds the wire of each of the legs 110, 110.

Further, the tension application unit 30 in the embodiments described above has used the electric motor 35 as the actuator. However, the actuator used by the tension application unit in the present invention is not limited to an electric motor, and a tension may be applied to the flexible lengthy member by a hydraulic actuator. Further, the actuator of the tension application unit is not limited to a rotary actuator and may be a linear motion actuator.

Further, the tension application unit in the present invention may be configured by using a locking mechanism capable of switching between a lock state in which the flexible lengthy member is mechanically locked and an unlock state in which the lock is cleared.

An example of the tension application unit will be described with reference to FIG. 14. A tension application unit 120 of the illustrated example includes, in a chassis 121, a locking mechanism 122 and a spring 123 serving as a pre-tension generating unit for applying a pre-tension to the wire 16 (hereinafter referred to as the pre-tension spring 123).

The tension application unit 120 can be applied to any one of the zigzag structures 13, 68, 81, 85, 91 and 101 described above. For the sake of convenience, however, the zigzag structure in the following description will be the zigzag structure 13 having the structure described in the first embodiment.

The locking mechanism 122 has a guide rail 124, a rack 125 slidable along the guide rail 124 (in other words, a movable section with projections and recessions arranged on the upper surface thereof), a hook piece 126 which engages/disengages the rack 125, a spring 127 for causing the hook piece 126 to engage/disengage the rack 125, and electromagnetic actuator 128.

A wire 16 as the flexible lengthy member is connected to one end of the rack 125, and the wire 16 is led out from the chassis 121 through a hole 121a formed in a side wall of the chassis 121. Further, the end of the wire 16 led out of the chassis 121 is connected to the first member 11 via the second member 12.

The pre-tension spring 123 is connected to the other end of the rack 125. The pre-tension spring 123 is provided between the other end of the rack 125 and the side wall of the chassis 121, and urges the rack 125 in a direction for pulling the wire 16 into the chassis 121 (leftward in FIG. 14).

The middle portion of the hook piece 126 between the distal portion (the tip of the hook) thereof and a rear end portion thereof is rotatably journaled by the distal portion of a support member 129 extended from the side wall of the chassis 121. The rotation axis is an axis in the direction that traverses the rack 125, i.e. the direction perpendicular to the paper surface in FIG. 14. Further, the hook piece 126 is capable of switching the operation thereof between a state in which the distal portion thereof, i.e. the tip of the hook, fits in the recession of the rack 125 as the hook piece 126 rotates (in a state in which the hook piece 126 has slightly rotated counterclockwise from the illustrated state) and a state in which the distal portion thereof disengages the recession (in a state in which the hook piece 126 has rotated clockwise from the illustrated state).

Figure 14:
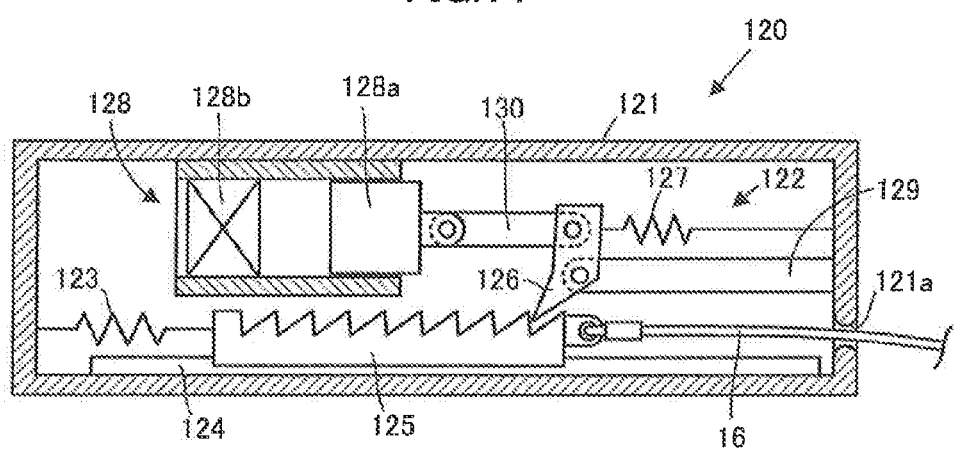
FIG. 14 is a diagram illustrating the configuration of another example of the tension application unit.

In the locking mechanism 122 illustrated in FIG. 14, the state in which the distal portion of the hook piece 126 has fitted in the recession of the rack 125 indicates a lock state in which the rack 125 has been locked to consequently lock the wire 16 thereby to block the rack 125 from traveling in the direction (rightward in FIG. 14) for pulling the wire 16 out of the chassis 121 (so as to block the wire 16 from traveling with respect to the second member 12 to cause the first member 11 to move away from the second member 12). Further, the state in which the distal portion of the hook piece 126 has disengaged the recession of the rack 125 is an unlock state.

The slope surface of the recession of the rack 125 is formed such that the hook piece 126 automatically rotates as the rack 125 travels so as to clear the lock state even if the distal portion of the hook piece 126 has fitted in the recession of the rack 125 in the case where the rack 125 travels in the direction for pulling the wire 16 into the chassis 121 by the urging force of the pre-tension spring 123. Thus, the wire 16 is always subjected to the pre-tension from the elastic force of the pre-tension spring 123.

The spring 127 is a spring that applies a rotational driving force for setting the locking mechanism 122 to the unlock state (a rotational driving force in the clockwise direction in FIG. 14) to the hook piece 126 by the elastic force (hereinafter referred to as the unlocking spring 127). The unlocking spring 127 is connected to the rear end of the hook piece 126. Further, the unlocking spring 127 provided between the hook piece 126 and the side wall of the chassis 121 urges the hook piece 126 in the clockwise direction in FIG. 14. Thus, the unlocking spring 127 urges the hook piece 126 to disengage the distal portion of the hook piece 126 from a recession of the rack 125.

The electromagnetic actuator 128 is an actuator for rotationally driving the hook piece 126 (rotationally driving the hook piece 126 in the counterclockwise direction in FIG. 14) to set the locking mechanism 122 to the lock state.

The electromagnetic actuator 128 includes a movable iron core 128a, which is slidable in the same direction as the sliding direction of the rack 125, and an electromagnet 128b, which generates an electromagnetic force for attracting the movable iron core 128a by being energized. The movable iron core 128a is disposed such that the hook piece 126 is placed between the movable iron core 128a and the unlocking spring 127. Further, the electromagnet 128b is disposed, facing the movable iron core 128a on the opposite side from the hook piece 126.

Further, the movable iron core 128a is attracted by the electromagnet 128b against the elastic force of the unlocking spring 127 by the electromagnetic force generated by energizing the electromagnet 128b, thus rotationally driving the hook piece 126 in the counterclockwise direction in FIG. 14. This causes the distal portion of the hook piece 126 to fit in a recession of the rack 125 so as to set the locking mechanism 122 to the lock state.

The tension application unit 120 illustrated in FIG. 14 is constructed as described above.

In the tension application unit 120, the operation control is carried out, for example, as described below. In a state in which a leg of a person on the same side (the right side or the left side) as the leg 3 having the zigzag structure 13 has become a swing leg, the electromagnetic actuator 128 is set to the OFF state, i.e. the supply of current to the electromagnet 128b is cut off. At this time, the distal portion of the hook piece 126 is disengaged from the recession of the rack 125 by the elastic force of the unlocking spring 127, thus setting the locking mechanism 122 to the unlock state. At this time, only a weak tension, namely, a pre-tension, is applied to the wire 16 by the pre-tension spring 123.

Hence, the zigzag structure 13 smoothly deforms to bend according to the relative displacement of the first member 11 and the second member 12 as the leg of the person, which has become the swing leg, bends or stretches.

Further, in the state in which the leg of the person on the same side as the leg 3 has become a supporting leg, the electromagnetic actuator 128 is set to the ON state, i.e. the state in which the electromagnet 128b is energized. Thus, the locking mechanism 122 is held in the lock state, in which the hook piece 126 is fitted in the recession of the rack 125. This blocks the rack 125 from moving in the direction for pulling the wire 16 out of the chassis 121 (so as to block the wire 16 from traveling with respect to the second member 12 to cause the first member 11 to move away from the second member 12), thus restricting the distance between the first member 11 and the second member 12 (the distance along the wire 16).

As a result, when the zigzag structure 13 starts to be bent, the tension applied to the wire 16 increases. In addition, the zigzag structure 13 generates a relatively large elastic force, i.e. the elastic force acting to cancel the bending of the zigzag structure 13, between the first member 11 and the second member 12.

This arrangement causes a force in the direction for stretching the supporting leg to be applied to the supporting leg when the person bends the supporting leg (lowers his or her waist).

Further, if a slack occurs in the wire 16, the pre-tension is applied to the wire 16 by the pre-tension spring 123 independently of the operation state of the locking mechanism 122. This eliminates the slack from the wire 16.

As described above, in the case where the tension application unit 120 having the configuration illustrated in FIG. 14 is used, when the zigzag structure 13 is bent, an elastic force that functions to cancel the bending can be also generated in the zigzag structure 13 as necessary, as with the first embodiment and the like.

In the tension application unit 120 illustrated in FIG. 14, the hook piece 126 is rotated to switch between the lock state and the unlock state of the locking mechanism 122. Alternatively, however, the hook piece or a pin may be directly operated to engage/disengage a recession of a member, such as the rack 125, thereby switching the operation state of the locking mechanism.

Further, the locking mechanism may alternatively be configured to mechanically lock and unlock a rotating member, such as a pulley, which rewinds and pulls out a flexible lengthy member, such as the wire 16.

Further, in the walking assist devices according to the embodiments or modifications described above, the first member 11 or 66 has been attached to the crus of a leg of a person through the intermediary of the lower frame 7, and the second member 12 or 67 has been attached to the thigh of a leg of the person through the intermediary of the upper frame 6. Alternatively, however, the first member 11 or 66 may be rotatably attached to a foot of the person or the second member 12 or 67 may be rotatably attached to the waist of the person.

Further, in the embodiments or the modifications described above, the descriptions have been given of the examples in which the joint mechanism in accordance with the present invention has been applied to the walking assist device. The joint mechanism in accordance with the present invention, however, can be also applied to, for example, a device adapted to assist a person with bending and stretching his or her arms or a device adapted to assist a person with bending and stretching his or her upper body, rather than being limited to the application to a walking assist device. Further, the joint mechanism in accordance with the present invention may be applied to a robot or the like.

What is claimed is:

1. A joint mechanism that connects a first member and a second member in a relatively displaceable manner, comprising:
a zigzag structure comprising at least one of a metal member and a resin member, the zigzag structure formed between the first member and the second member such that the zigzag structure extends from the first member toward the second member in a zigzag pattern having an amplitude in a lateral direction, the zigzag structure having an end portion thereof adjacent to the first member and an end portion thereof adjacent to the second member connected to the first member and the second member, respectively, the zigzag structure includes a plurality of connected element members, each of the element members is composed of a plate-like elastic member and includes a top portion and a pair of leg portions which are integrally formed at proximal ends with the top portion and extend in a bifurcated manner from the top portion, wherein each of a pair of opposing edges of a first plate member of the plate-like elastic member composing the top portion and each of edges of a pair of second plate members of the plate-like elastic member respectively composing the pair of leg portions are consecutive, and faces of the pair of second plate members respectively composing the pair of leg portions are opposed to each other, wherein distal ends of leg portions of adjacent element members are connected, and the zigzag structure is deformably configured to allow a length in a direction of an amplitude centerline thereof and a bending degree of the amplitude centerline to be changed, wherein the zigzag structure is biased by its own elasticity so that, when the zigzag structure is deformed, the length of the zigzag structure in the direction of the amplitude centerline is biased to return to a predetermined original length and the bending degree of the amplitude centerline is biased to return to a predetermined original bending degree;
a flexible lengthy member which is disposed to extend from the first member toward the second member, which has one end portion adjacent to the first member fixed to the first member, which is provided to be travelable with respect to the second member, and which applies a force for pressing the zigzag structure between the first member and the second member to the zigzag structure in a state in which a tension is being applied, the flexible lengthy member being disposed to extend at a position adjacent to a top side in the lateral direction of the zigzag structure; and
a tension application unit which is a device for applying the tension to the flexible lengthy member from a side of the other end portion of the flexible lengthy member and which is configured to be capable of changing a magnitude of the tension,
wherein an inter-leg-portion elastic member is provided between each pair of leg portions, which extend in the bifurcated manner from each top portion located on one side in the lateral direction of the zigzag structure,
wherein the inter-leg-portion elastic member is configured such that, upon bending deformation of the zigzag structure in a manner that each of the top portions composing each of the element members separate from each other and also in a manner that the distal ends of the pair of leg portions composing each of the element members approach each other in a state in which a tension of a predetermined value or more is being applied to the flexible lengthy member by at least the tension application unit, the inter-leg-portion elastic member is compressed between the pair of leg portions at a bottom side in the lateral direction of the zigzag structure thereby to generate an elastic force that functions to cancel the bending deformation of the zigzag structure, and
wherein the flexible lengthy member is disposed at an opposite side of the inter-leg-portion elastic member with respect to the top portion.

2. The joint mechanism according to claim 1,
wherein the inter-leg-portion elastic member is composed of a first elastic member made of rubber that is firmly fixed to one leg portion of the pair of leg portions on both sides thereof and a second elastic member made of rubber that is firmly fixed to the other leg portion so as to oppose the first elastic member, and the first elastic member and the second elastic member are compressed in contact with each other upon being compressed between the pair of leg portions.

3. The joint mechanism according to claim 1,
wherein the inter-leg-portion elastic member is provided between the pair of leg portions extending in the bifurcated manner from each of the plurality of top portions positioned on one side in the amplitude direction of the zigzag structure, and a stiffness or an arrangement of the inter-leg-portion elastic member corresponding to each of the plurality of top portions is set such that, upon bending deformation of the zigzag structure such that one side in the lateral direction thereof is placed on an outer side and the other side thereof is placed on an inner side, a strain of the inter-leg-portion elastic member corresponding to each of the plurality of top portions positioned on one side in the lateral direction of the zigzag structure approximates to uniformity with each other.

4. The joint mechanism according to claim 1,
wherein a stopper member that prevents an interval of the pair of leg portions from becoming smaller than a predetermined amount is fixedly installed to at least one of the pair of leg portions for each of top portions positioned on one side in the lateral direction of the zigzag structure.

5. The joint mechanism according to claim 4,
wherein the stopper member corresponding to each top portion positioned on one side in the lateral direction of the zigzag structure is composed of a pair of stopper members fixedly installed, opposing the pair of leg portions extending in the bifurcated manner from the top portion, and the pair of stopper members is configured to come in contact with each other and a recession formed in one of the pair of stoppers and a projection formed on the other thereof fit each other in the case where an interval between the pair of leg portions on both sides thereof reduces to a predetermined amount.

6. The joint mechanism according to claim 1, wherein each plate-like elastic member has a width in a direction orthogonal to the lateral direction of the zigzag structure and the direction of the amplitude centerline and is formed into a U shape or a rectangular shape having the top portion and the pair of leg portions extending in the bifurcated manner from the top portion, the plurality of element members are placed such that the top portions thereof are arranged in the direction of the amplitude centerline as the top portions positioned on one side in the lateral direction of the zigzag structure, and further, in a case where one of the element members of a pair of adjacent element members is denoted as a first element member and the other element member of the pair of adjacent element members is denoted as a second element member, a distal end of a first A leg portion, which is a leg portion of a pair of leg portions of the first element member that is on a side of the second element member, and a distal end of a second A leg portion, which is a leg portion of a pair of leg portions of the second element member that is on a side of the first element member, are connected into one piece, and a portion connecting the distal end of the first A leg portion and the distal end of the second A leg portion provides each top portion positioned on the other side in the amplitude direction of the zigzag structure, and the zigzag structure is configured such that the first A leg portion of the first element member and the second A leg portion of the second element member come in contact with each other in a state in which a tension of a predetermined value or more is being applied to the flexible lengthy member by the tension application unit.

7. The joint mechanism according to claim 1, further comprising:
a cover member that has a pair of cover surfaces disposed to cover both side surfaces of the zigzag structure in a direction of thickness of the zigzag structure, which is a direction orthogonal to the lateral direction of the zigzag structure and the direction of the amplitude centerline, an interval being provided between the pair of cover surfaces in the direction of thickness,
wherein deformation of the zigzag structure is restricted to a deformation within the interval of the pair of cover surfaces of the cover member.

8. The joint mechanism according to claim 7, wherein the cover member is configured to bend as the zigzag structure is deformed to bend within the interval of the pair of cover surfaces of the cover member.

9. A joint mechanism that connects a first member and a second member in a relatively displaceable manner, comprising:
a zigzag structure which is configured to extend between the first member and the second member in a zigzag pattern from the first member toward the second member and have an amplitude in a lateral direction, an end portion thereof adjacent to the first member and an end portion thereof adjacent to the second member being connected to the first member and the second member, respectively, the zigzag structure includes a plurality of connected element members, each of the element members is composed of a plate-like elastic member and includes a top portion and a pair of leg portions which are integrally formed at proximal ends with the top portion and extend in a bifurcated manner from the top portion, wherein each of a pair of opposing edges of a first plate member of the plate-like elastic member composing the top portion and each of edges of a pair of second plate members of the plate-like elastic member respectively composing the pair of leg portions are consecutive, and faces of the pair of second plate members respectively composing the pair of leg portions are opposed to each other, wherein distal ends of leg portions of adjacent element members are connected, and which is configured to be deformable such that a length in a direction of an amplitude centerline of the zigzag structure and a bending degree of the amplitude centerline can be changed by the pair of leg portions, which extends in the bifurcated manner from each top portion positioned on each of both sides in the lateral direction of the zigzag structure, and which is relatively rotatably connected about an axis of a support shaft through the intermediary of the support shaft, which has an axis orthogonal to the lateral direction of the zigzag structure and the direction of the amplitude centerline and which is provided on the top portion, wherein the zigzag structure comprises at least one of a metal member and a resin member, the zigzag structure is biased by its own elasticity so that when the zigzag structure is deformed, the length of the zigzag structure in the direction of the amplitude centerline is biased to return to a predetermined original length and the bending degree of the amplitude centerline is biased to return to a predetermined original bending degree;

an inter-leg-portion elastic member which is provided between the pair of leg portions extending in the bifurcated manner from each top portion positioned on each of both sides in the lateral direction of the zigzag structure and which is compressed and generates an elastic force as an interval of the pair of leg portions decreases, the inter-leg-portion elastic member being configured such that, upon bending deformation of the zigzag structure in a manner that each of the top portions composing each of the element members separate from each other and also in a manner that the distal ends of the pair of leg portions composing each of the element members approach each other in a state in which a tension of a predetermined value or more is being applied to the flexible lengthy member by at least the tension application unit, the inter-leg-portion elastic member is compressed between the pair of leg portions at a bottom side in the lateral direction of the zigzag structure thereby to generate an elastic force that functions to cancel the bending deformation of the zigzag structure;

a flexible lengthy member which is disposed to extend from the first member toward the second member, which has one end portion adjacent to the first member fixed to the first member, which is provided to be travelable with respect to the second member, and which applies, to the zigzag structure, a force for pressing the zigzag structure between the first member and the second member in a state in which a tension is being applied, the flexible lengthy member being disposed to extend at a position adjacent to a top side in the lateral direction of the zigzag structure, and the flexible lengthy member is disposed at an opposite side of the inter-leg-portion elastic member with respect to the top portion; and a tension application unit which applies the tension to the flexible lengthy member from a side of the other end portion of the flexible lengthy member and which is configured to be capable of changing the magnitude of the tension.

10. The joint mechanism according to claim 9, wherein the inter-leg-portion elastic member is composed of a first elastic member made of rubber that is firmly fixed to one leg portion of the pair of leg portions on both sides thereof and a second elastic member made of rubber that is firmly fixed to the other leg portion so as to oppose the first elastic member, and the first elastic member and the second elastic member are compressed in a state of being in contact with each other when compressed between the pair of leg portions.

11. The joint mechanism according to claim 9, wherein the inter-leg-portion elastic member is provided between the pair of leg portions extending in the bifurcated manner from each top portion positioned on one side in the lateral direction of the zigzag structure, and a stiffness or an arrangement of the inter-leg-portion elastic member corresponding to each top portion is set such that, upon bending deformation of the zigzag structure such that one side in the lateral direction thereof is placed on an outer side and the other side thereof is placed on an inner side, a strain of the inter-leg-portion elastic member corresponding to each top portion positioned on one side in the lateral direction of the zigzag structure approximates to uniformity with each other.

12. The joint mechanism according to claim 1, wherein the first member and the second member are members configured to be attached to a crus or a foot of a leg of a person and a thigh or waist, respectively, in a state in which the zigzag structure is positioned on the side of a knee joint of the leg of the person.

13. The joint mechanism according to claim 9, wherein the first member and the second member are members configured to be attached to a crus or a foot of a leg of a person and a thigh or waist, respectively, in a state in which the zigzag structure is positioned on the side of a knee joint of the leg of the person.

14. The joint mechanism according to claim 1, wherein the tension application unit comprises an actuator which generates a driving force for applying the tension to the flexible lengthy member, and a brake unit which is provided in a power transmission system between the actuator and the flexible lengthy member and which is capable of operating in a state in which a travel motion of the flexible lengthy member is braked and a state in which braking is cleared.

15. The joint mechanism according to claim 9, wherein the tension application unit comprises an actuator which generates a driving force for applying the tension to the flexible lengthy member, and a brake unit which is provided in a power transmission system between the actuator and the flexible lengthy member and which is capable of operating in a state in which a travel motion of the flexible lengthy member is braked and a state in which braking is cleared.

16. The joint mechanism according to claim 1, wherein the tension application unit comprises an actuator which generates a driving force for applying the tension to the flexible lengthy member and a clutch unit which is capable of operating in a state in which power transmission between the actuator and the flexible lengthy member is cut off and a state in which the power transmission is carried out.

17. The joint mechanism according to claim 9, wherein the tension application unit comprises an actuator which generates a driving force for applying the tension to the flexible lengthy member and a clutch unit which is capable of operating in a state in which the power transmission between the actuator and the flexible lengthy member is cut off and a state in which the power transmission is carried out.

18. The joint mechanism according to claim 14, wherein the tension application unit further comprises a pre-tension generating unit which applies a pre-tension, which is an anti-slack tension for preventing a slack of the flexible lengthy member, to the flexible lengthy member.

19. The joint mechanism according to claim 15, wherein the tension application unit further comprises a pre-tension generating unit which applies a pre-tension, which is an anti-slack tension for preventing a slack of the flexible lengthy member, to the flexible lengthy member.

20. The joint mechanism according to claim 16, wherein the tension application unit further comprises a pre-tension generating unit which applies a pre-tension, which is an anti-slack tension for preventing a slack of the flexible lengthy member, to the flexible lengthy member.

21. The joint mechanism according to claim 17, wherein the tension application unit further comprises a pre-tension generating unit which applies a pre-tension, which is an anti-slack tension for preventing a slack of the flexible lengthy member, to the flexible lengthy member.

22. The joint mechanism according to claim 18, further comprising:
a one-way clutch mechanism which is provided between the actuator and the flexible lengthy member and which blocks transmission of a force in a direction in which the flexible lengthy member slacks.

23. The joint mechanism according to claim 19, further comprising:
a one-way clutch mechanism which is provided between the actuator and the flexible lengthy member and which blocks transmission of a force in a direction in which the flexible lengthy member slacks.

24. The joint mechanism according to claim 20, further comprising:
a one-way clutch mechanism which is provided between the actuator and the flexible lengthy member and which blocks transmission of a force in a direction in which the flexible lengthy member slacks.

25. The joint mechanism according to claim 21, further comprising:
a one-way clutch mechanism which is provided between the actuator and the flexible lengthy member and which blocks transmission of a force in a direction in which the flexible lengthy member slacks.

26. The joint mechanism according to claim 1, wherein the tension application unit comprises a locking mechanism capable of switching between a lock state in which the flexible lengthy member is locked so as to block the flexible lengthy member from traveling with respect to the second member in a direction in which the first member moves away from the second member and an unlock state in which the locking is cleared; and a pre-tension generating unit which applies a pre-tension, which is an anti-slack tension for preventing a slack of the flexible lengthy member, to the flexible lengthy member.

27. The joint mechanism according to claim 9, wherein the tension application unit comprises a locking mechanism capable of switching between a lock state in which the flexible lengthy member is locked so as to block the flexible lengthy member from traveling with respect to the second member in a direction in which the first member moves away from the second member and an unlock state in which the locking is cleared; and a pre-tension generating unit which applies a pre-tension, which is an anti-slack tension for preventing a slack of the flexible lengthy member, to the flexible lengthy member.

* * * * *